United States Patent
Pierceall et al.

(10) Patent No.: US 10,640,803 B2
(45) Date of Patent: May 5, 2020

(54) METHODS FOR DETERMINING CHEMOSENSITIVITY AND CHEMOTOXICITY

(71) Applicant: EUTROPICS PHARMACEUTICALS, INC., Cambridge, MA (US)

(72) Inventors: William E. Pierceall, Madison, NJ (US); Michael H. Cardone, Dorchester, MA (US)

(73) Assignee: Eutropics Pharmaceuticals, Inc., Cambridge, MA (US)

( * ) Notice: Subject to any disclaimer, the term of this patent is extended or adjusted under 35 U.S.C. 154(b) by 17 days.

(21) Appl. No.: 15/033,810

(22) PCT Filed: Oct. 30, 2014

(86) PCT No.: PCT/US2014/063121
§ 371 (c)(1),
(2) Date: May 2, 2016

(87) PCT Pub. No.: WO2015/066305
PCT Pub. Date: May 7, 2015

(65) Prior Publication Data
US 2016/0273020 A1   Sep. 22, 2016

Related U.S. Application Data

(60) Provisional application No. 61/897,547, filed on Oct. 30, 2013.

(51) Int. Cl.
*C12Q 1/02* (2006.01)
*C12Q 1/6886* (2018.01)

(52) U.S. Cl.
CPC .......... *C12Q 1/025* (2013.01); *C12Q 1/6886* (2013.01); *C12Q 2600/106* (2013.01); *G01N 2500/10* (2013.01)

(58) Field of Classification Search
None
See application file for complete search history.

(56) References Cited

U.S. PATENT DOCUMENTS

| | | |
|---|---|---|
| 5,856,445 A | 1/1999 | Korsmeyer |
| 5,955,593 A | 9/1999 | Korsmeyer |
| 5,998,583 A | 12/1999 | Korsmeyer |
| 6,165,732 A | 12/2000 | Korsmeyer et al. |
| 6,258,540 B1 | 7/2001 | Lo et al. |
| 6,326,354 B1 | 12/2001 | Gross et al. |
| 7,026,456 B1 | 4/2006 | Gately et al. |
| 7,247,700 B2 | 7/2007 | Korsmeyer et al. |
| 7,345,700 B2 | 3/2008 | Nortrup |
| 7,723,469 B2 | 5/2010 | Walensky et al. |
| 7,755,765 B2 | 7/2010 | Post et al. |
| 7,829,662 B2 | 11/2010 | Korsmeyer et al. |
| 7,868,133 B2 | 1/2011 | Korsmeyer et al. |
| 7,871,769 B2 | 1/2011 | Baker et al. |
| 8,168,755 B2 | 5/2012 | Cardone et al. |
| 8,198,405 B2 | 6/2012 | Walensky et al. |
| 8,221,966 B2 | 7/2012 | Letai |
| 8,323,987 B2 | 12/2012 | Threadgill et al. |
| 2002/0177692 A1 | 11/2002 | Bartel |
| 2003/0073661 A1 | 4/2003 | Matsuyama et al. |
| 2003/0181404 A1 | 9/2003 | Avraham et al. |
| 2004/0171890 A1 | 9/2004 | Korsmeyer et al. |
| 2004/0241902 A1 | 10/2004 | Wang et al. |
| 2005/0191696 A1 | 9/2005 | Goldmakher et al. |
| 2006/0183687 A1 | 8/2006 | Cory et al. |
| 2008/0104721 A1 | 5/2008 | Barsova et al. |
| 2008/0199890 A1 | 8/2008 | Letai |
| 2008/0300239 A1 | 12/2008 | Adams et al. |
| 2009/0005416 A1 | 1/2009 | Munchhof et al. |
| 2009/0030005 A1 | 1/2009 | Kamb et al. |
| 2009/0280510 A1 | 11/2009 | Cardone et al. |
| 2010/0015058 A1 | 1/2010 | Li et al. |
| 2011/0008371 A1 | 1/2011 | Michelson |
| 2011/0071042 A1 | 3/2011 | Kim et al. |
| 2011/0154522 A1 | 6/2011 | Korsmeyer et al. |
| 2011/0301193 A1 | 12/2011 | Errico et al. |
| 2012/0041070 A1 | 2/2012 | Jin et al. |
| 2012/0172371 A1 | 7/2012 | Pommier et al. |
| 2012/0196853 A1 | 8/2012 | Durrenberger et al. |
| 2012/0225794 A1 | 9/2012 | Cardone et al. |
| 2012/0225851 A1 | 9/2012 | Cardone et al. |

(Continued)

FOREIGN PATENT DOCUMENTS

| | | |
|---|---|---|
| CN | 1583776 A | 2/2005 |
| WO | 96/13614 A1 | 5/1996 |
| WO | 96/15263 A1 | 5/1996 |

(Continued)

OTHER PUBLICATIONS

Certo et al. "Mitochondria primed by death signals determine cellular addiction to antiapoptotic BCL-2 family members" Cancer Cell 9, 351-365, May 2006 (Year: 2006).*
Moore et al. "BH3 profiling—measuring integrated function of the mitochondrial apoptotic pathway to predict cell fate decisions" Cancer Lett. May 28, 2013; 332(2): 202-205, available online Sep. 11, 2013 (Year: 2013).*
Ryan et al. "Heightened mitochondrial priming is the basis for apoptotic hypersensitivity of CD4+ CD8+ thymocytes" PNAS | Jul. 20, 2010 | vol. 107 | No. 29 | 12895-12900 (Year: 2010).*
Lazaridou et al. "Simultaneous Detection of BCL-2 Protein, Trisomy 12, Retinoblastoma and P53 Monoallelic Gene Deletions in B-Cell Chronic Lymphocytic Leukemia by Fluorescence in Situ Hybridization (FISH): Relation to Disease Status" Leukemia & Lymphoma, 36:5-6, 503-512 (Year: 2000).*
Reed et al, Blood 2008, vol. 111, No. 7, pp. 3322-3330.
Strigacova et al., "Some Biological Properties of New Quinoline-4-carboxylic Acid and Quinoline-4 Carboxamide Derivatives", Folia Microbiol (Praha) 2000, 45(4):305-9.

(Continued)

*Primary Examiner* — Blaine Lankford
(74) *Attorney, Agent, or Firm* — Morgan, Lewis & Bockius LLP

(57) ABSTRACT

The present disclosure relates to diagnostic methods that are relevant to various cancers and which comprise BH3 profiling diagnostics for, among others, predication of an adverse patient response to a cancer treatment.

14 Claims, 10 Drawing Sheets

(56) References Cited

U.S. PATENT DOCUMENTS

2013/0079424 A1 3/2013 Gerber et al.

FOREIGN PATENT DOCUMENTS

| WO | 1998/009643 A1 | 3/1998 |
|---|---|---|
| WO | 1998/009980 A1 | 3/1998 |
| WO | 1998/017682 A1 | 4/1998 |
| WO | 1999/016787 A9 | 4/1999 |
| WO | 2000/006187 A2 | 2/2000 |
| WO | 2000/011162 A1 | 3/2000 |
| WO | 2011/020886 A1 | 2/2001 |
| WO | 2002/005835 A1 | 1/2002 |
| WO | 2003/057158 A2 | 7/2003 |
| WO | 2004/022580 A2 | 3/2004 |
| WO | 2004/066958 A2 | 8/2004 |
| WO | 2004/074218 A2 | 9/2004 |
| WO | 2004/080463 A1 | 9/2004 |
| WO | 2004/087887 A2 | 10/2004 |
| WO | 2005/028444 A1 | 3/2005 |
| WO | 2005/044839 A2 | 5/2005 |
| WO | 2005/049576 A1 | 6/2005 |
| WO | 2007/123791 A9 | 1/2007 |
| WO | 2008/021484 A1 | 2/2008 |
| WO | 2010/042163 A2 | 4/2010 |
| WO | 2010/093742 A1 | 8/2010 |
| WO | 2010/107765 A1 | 9/2010 |
| WO | 2010/143168 A2 | 12/2010 |
| WO | 2011/085126 A2 | 7/2011 |
| WO | WO 2011/088137 A2 | 7/2011 |
| WO | 2011/094708 A2 | 8/2011 |
| WO | 2011/127333 A2 | 10/2011 |
| WO | 2012/012653 A1 | 1/2012 |
| WO | WO 2012/122370 A2 | 9/2012 |
| WO | 2013/138702 A2 | 9/2013 |

OTHER PUBLICATIONS

Yamanaka et al., Molecular Cancer Ther., 2005, vol. 4, No. 11, pp. 1689-1698.
Yang et al., Cancer Research, vol. 63, 2003, pp. 6815-6824.
KG-la (ATCC® CCL-246.1™) ATCC Product Sheet, 3 pages (2013).
Adlard, et al., "Prediction of the response of colorectal cancer to systemic therapy," Lancet Oncol. 3:75-82 (2002).
Bodet, et al., "BH3-only protein Bik is involved in both apoptosis induction and sensitivity to oxidative stress in multiple myeloma," Br. J. Cancer 103:1808-1814 (2010).
Campbell, et al., "General properties and applications of monoclonal antibodies," Monoclonal Antibody Technology, pp. 1-32 (1984).
Certo, et al., "Mitochondria Primed by Death Signals Determine Cellular Addiction to Antiapoptotic BCL-2 Family Members," Cancel Cell 9:351-365 (May 2006).
Chonghaile, et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1142, 53rd ASH Annual Meeting and Exposition, Dec. 10-13, 2011, American Society of Hematology.
Chonghaile, et al., "Pretreatment Mitochondrial Priming Correlates with Clinical Response to Cytotoxic Chemotherapy," Science 334:1129-1133, including supporting material (2011).
Cimmino, et al., "miR-15 and miR-16 induce apoptosis by targeting BCL2," Proc. Natl. Acad. Sci. USA 102 (39):13944-13945 (2005).
Colman, "Effects of amino acid sequence changes on antibody-antigen interactions," Res. Immunol. 145"33-36 (1994).
Davids, et al., "BH13 Profiling Demonstrates That Restoration of Apoptotic Priming Contributes to Increased Sensitivity to PI3K Inhibition on Stroma-Exposed Chronic Lymphocytic Leukemia Cells," Blood 118: Abstract 974 (2011).
Del Gaizo Moore, et al., "BH3 profiling—measuring intergrated function of the mitochondrial apoptotic to predict cell fate decisions," Cancer Lett. 332(2):202-205 (2013).
Del Gaizo Moore, et al., "Chronic lymphocytic leukemia requires BCL2 to sequester prodeath BIM, explaining sensitivity to BCL2 antagonist ABT-737," J. Clin. Invest. 117(1):112-121 (2007).
Deng, et al., "BH3 Profiling Identifies Three Distinct Classes of Apoptotic Blocks to Predict Response to ABT-737 and Conventional Chemotherapeutic Agents," Cancel Cell 12:171-185 (2007).
Hann, et al., "Therapeutic Efficacy of ABT-737, a Selective Inhibitor of BCL-2, in Small Cell Lung Cancer," Cancer Res. 68:2321-2328 (2008).
Kasper, et al., "Targeting MCL-1 sensitizes FLT3-ITD-positive leukemias to cytotoxic therapies," Blood Cancer J. 2:10 pages (2012).
Letai, et al., "Antiapoptotic BCL-2 is required for maintenance of a model leukemia," Cancer Cell, 6:241-249 (2004).
Letai, et al., "Diagnosing and exploiting cancer's addiction to blocks in apoptosis," Nat. Rev. Cancer 8:121-132 (2008).
Maccallum et al., "Antibody-antigen Interactions: Contact Analysis and Binding Site Topography," J. Mol. Biol. 262:732-745 (1996).
Miller, et al, "Therapeutic Strategies to Enhance the Anticancer Efficacy of Histone Deacetylase Inhibitors," J. Biomed. Biotechnol. 2011:17 pages (2011).
Paoluzzi, et al., "The BH3-only mimetic ABT-737 synergizes the antineoplastic activity of proteasome inhibitors in lymphoid malignancies," Blood 112:2906-2916 (2008).
Paul, "Fundamental Immunology," 3rd Edition, Raven Press, Ltd., pp. 292-295 (1993).
Pierceall, et al., "BH3 Profiling Discriminates Response to Cytarabine-Based Treatment of Acute Myelogenous Leukemia," Mol. Cancer Ther. 12(12):2940-2949 (2013).
Pode-Shakked, et al., "Developmental tumourigenesis: NCAM as a putative marker for the malignant renal stem/progenitor cell population," J. Cell. Mol. Med. 13(88):1792-1808 (2009).
Pritzker, et al., "Cancer Biomarkers: Easier Said Than Done," Clin. Chem. 48(8):1147-1150 (2002).
Raychaudhuri, et al., "Low probability Bid-Bax reaction generates heterogeneit in apoptosis resistance of cancer and cancer stem cells," arXiv:1108.209 [q-bio.MN], 17 pages (2011).
Rollins-Raval and Roth, "The value of immunohistochemistry for CD14, CD123, CD33, myeloperoxidase and CD68R in the diagnosis of acute and chronic myelomonocytic leukaemias," Histopathology 60:933-942 (2012).
Rudikoff, et al., "Single amino acid substitution altering antigen-binding specificity," Proc. Natl. Acad. Sci. USA 79:1979-1983 (1982).
Sinicrope, et al., "Proapoptotic Bad and Bid Protein Expression Predict Survival in Stages II and III Colon Cancers," Clin. Canc. Res. 14(13):4128-4133 (2008).
Sinicrope, et al., "Prognostic Impact of Bim, Puma, and Noxa Expression in Human Colon Carcinomas," Clin. Canc. Res. 14(18):5810-5818 (2008).
Stewart, et al., "The MCL-1 BH3 Helix is an Exclusive MCL-1 inhibitor and Apoptosis Sensitizer," Nat. Chem. Biol. 6(8):595-601 (2010).
Taussig, et al., "Anti-CD38 antibody-mediated clearance of human repopulating cells masks the heterogeneity of leukemia-initiating cells," Blood 112:568-575 (2008).
Thomenius, et al., "Using BH3 Profiling as a Predictive Indicator for Myeloma Patient Response to Bortezomib," Blood 118(21):abstract No. 3952 (2011).
Valencia, et al., "A new reliable fluorescence in situ hybridization method for identifying multiple specific cytogenetic abnormalities in acute myeloid leukemia," Leukemia & Lymphoma 51(4):680-685 (2010).
Vo, "Mitchondrial Priming Determines Chemotherapeutic Response in Acute Myeloid Leukemia," Disseration, Harvard University, UMI No. 3514220, 119 pages (2012).
Vo, "Relative Mitochondrial Priming of Myeloblasts and Normal HCSs Detemines Chemotherapeutic Success in AML," Cell 151(2):344-355 (2012).
Weniger, et al., "Treatment-Induced Oxidative Stress and Cellular Antioxidant Capacity Determine Response to Bortezomib in Mantel Cell Lymphoma," Clin. Canc. Res. 17(15):5101-5112 (2011).

(56) References Cited

OTHER PUBLICATIONS

Liu, et al., "The Structure of a Bcl-xL/Bim Fragment Complex: Implications for Bim Function," Immunity, vol. 19, 341-352, Sep. 2003.
Mohammad et al., "Nonpeptidic Small-Molecule Inhibitor of Bcl-2 and Bcl-XL, (-31)-Gossypol, Enhances Biological Effect of Genistein Against BxPC-3 Human Pancreatic Cancer Cell Line," Pancreas, vol. 31, No. 4, Nov. 2005, pp. 317-324.
Bellows et al., Journal of Virology, Jun. 2000, vol. 74, No. 11, pp. 5024-5031.
Bhat, S. et al., "Substituted Oxines Inhibit Endothelial Cell Proliferation and Angiogenesis", Organic & Biomolecular Chemistry (2012) 10(15):2979-2992.
Combaret, V. et al., Effect of Bortezomib on Human Neuroblastoma: Analysis of Molecular Mechanisms Involved in Cytotoxicity, Molecular Cancer, Jun. 5, 2008, vol. 7, No. 50; DOI:10.1186/1476-4598-7-50.
Fidler, Tumor Heterogeneity and the Biology of Cancer Invasion andMetastasis, (Cancer Res 1978; 38:2651-2660).
Lupo, B. et al. "Lenalidomide in the Treatment of Young Patients with Multiple Myeloma: From Induction to Consolidation/Maintenance Therapy", Advances in Hematology, Jul. 11, 2012, vol. 2012, ID No. 906247, pp. 1-6.
Neidle, Stephen, ed. :Cancer Drug Design and Discover, Elsevier/Academic Press, 2008, p. 431.
Patani and Lavoie, "Bioisosterism: A Rational Approach in Drug Design", Chem. Rev. 1996, 96, 3147-3176.
PUBCHEM Compound ID 49790728, Create Date Dec. 15, 2010 (online), retrieved on Aug. 3, 2012; http://pubchem.ncbi.nim.nih.gov/sumary/summary.cgi?cid+49790728.
Qin, Jie et al., "Identification of a Novel Family of BRAFV600E Inhibitors", J. Med. Chem. 2012, 55(11):5220-5230.
International Search Report, PCT appl. No. PCT/US2014/063121, 3 pages (dated Feb. 10, 2015).
Written Opinion of the International Searching Authority, PCT appl. No. PCT/US2014/063121, 5 pages (dated Feb. 10, 2015).

* cited by examiner a) CLL PBMC specimen prior to magnetic separation.
b) Post-purification CLL B cells

METHODS FOR DETERMINING CHEMOSENSITIVITY AND CHEMOTOXICITY

FIELD OF THE INVENTION

The present disclosure relates to methods that are useful in evaluating tumors in human samples.

BACKGROUND

The use of predictive and prognostic biomarkers paired with targeted cancer therapies may hold the key to reducing drug development time, improving drug efficacy, and guiding clinical decision making. While there have been advances in cancer treatment, chemotherapy remains largely inefficient and ineffective. One reason for the generally poor performance of chemotherapy is that the selected treatment is often not closely matched to the individual patient's disease. A personalized medicine approach that couples precise diagnostics with therapeutics might alleviate this problem.

Further complicating widespread application of chemotherapies is that subsets of patients are likely to incur life-threatening treatment-related toxicities. For example, tumor lysis syndrome (TLS) may cause a patient to be unable to receive a treatment for its cancer. Again, personalized medicine approaches seek to improve clinical outcomes by identifying patients likely to exhibit such toxicities and eliminate them from consideration for treatments likely to exhibit said toxicity.

Diagnostic approaches are needed that can predict drug toxicity, including susceptibility to TLS, and drug efficacy in a patient.

SUMMARY OF THE INVENTION

Accordingly, in one aspect, the present disclosure provides a method for determining an adverse response to one or more cancer treatments in a patient, comprising: determining a BH3 profile for the patient's cell specimen; and classifying the patient for likelihood of an adverse response to one or more cancer treatments, in some embodiments, the method for determining an adverse response to one or more cancer treatments in a patient comprises a) isolating a cancer cell or specimen from the patient; b) contacting the cancer cell or specimen with one or more BH3 peptides; c) detecting a signal that indicates mitochondrial membrane permeabilization, e) determining a correlation between the mitochondrial membrane permeabilization and adverse events from treatment; and f) classifying the patient for likelihood to adverse events from treatment.

In another aspect, the present disclosure provides a method for determining a treatment response to one or more cancer treatments in a blood cancer patient, comprising: determining a BH3 profile for the patient's tumor or cancer cell specimen; and classifying the patient for likelihood of one or more of an adverse response to one or more cancer treatments and a therapeutic efficacy to one or more cancer treatments wherein a BH3 profile comprising BAD and/or PUMA is indicative of an adverse response to one or more cancer treatments and a BH3 profile comprising BIM and/or HRK is indicative of therapeutic efficacy to one or more cancer treatments. In some embodiments, the method for determining a treatment response to one or more cancer treatments in a patient comprises a) isolating a cancer cell or specimen from the patient; h) contacting the cancer cell or specimen with one or more BH3 peptides; c) detecting a signal that indicates mitochondrial membrane permeabilization; e) determining a correlation between the mitochondrial membrane permeabilization and adverse response to one or more cancer treatments and a therapeutic efficacy to one or more cancer treatments; and f) classifying the patient for likelihood to adverse response to one or more treatments and therapeutic efficacy to one or more cancer treatments. In some embodiments, mitochondrial membrane permeabilization after contacting the cancer cell or specimen with BAD and/or PUMA is indicative of an adverse response to one or more cancer treatments, and mitochondrial membrane permeabilization after contacting the cancer cell or specimen with BIM and/or HRK (is indicative of therapeutic efficacy to one or more cancer treatments. The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

Table 1 shows CLL patient clinical pathologic information. Patient characteristics were analyzed relative to response (either response given as 3 groups (PD, SD, PR) or as two groups (PD, SD). Only trisomy 12 was indicated to be statistically significant for response and this was later used as an adjustment variable in layered predictive modeling.

Table 2 shows BH3 profiling biomarkers discriminate clinical response to alvocidib treatment. CLL patients were divided into training and test cohorts and assayed independently blinded to outcomes. Both training (n=30) and test cohorts (n=32) displayed significance for regression p-values for Bim (0.1) and (Hrk) indicating each may be predictive of therapeutic response. In the combined data sets for all patients. Hit is shown to display greatest predictive capacity and Bim (0.1) carries significance as well.

Figure 2A:
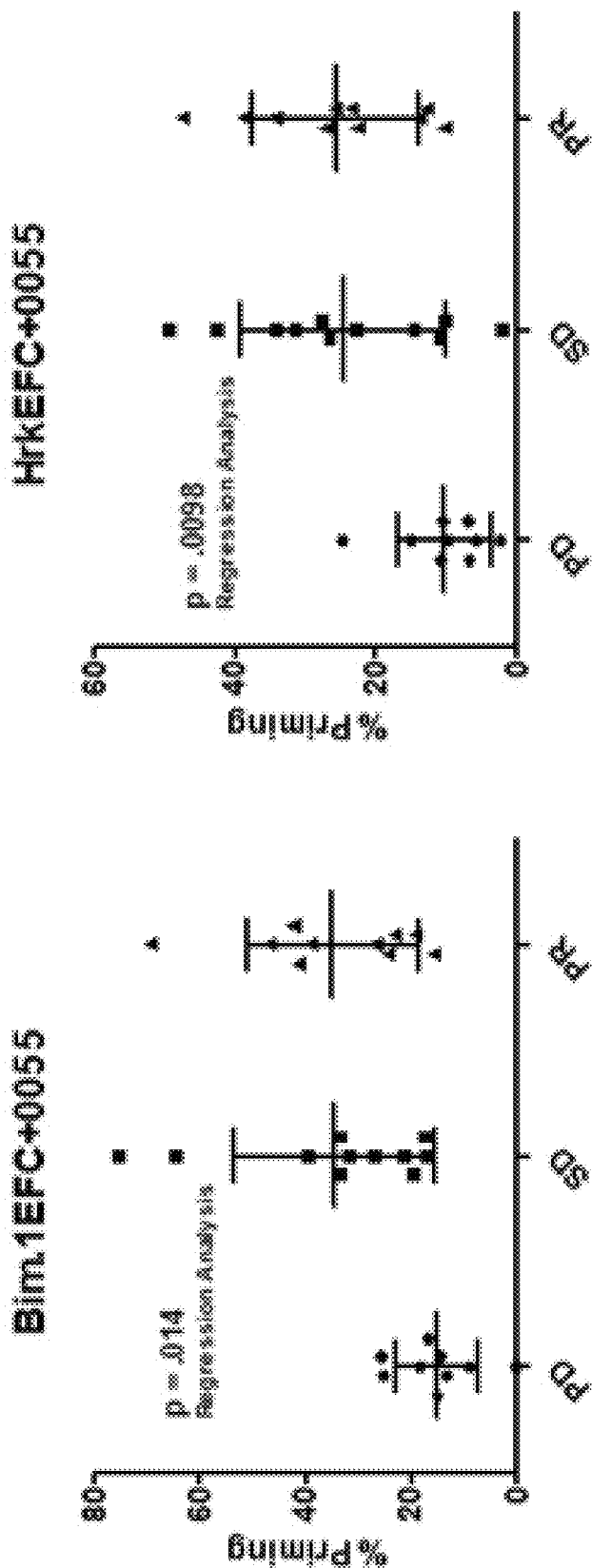
Figure 2B:
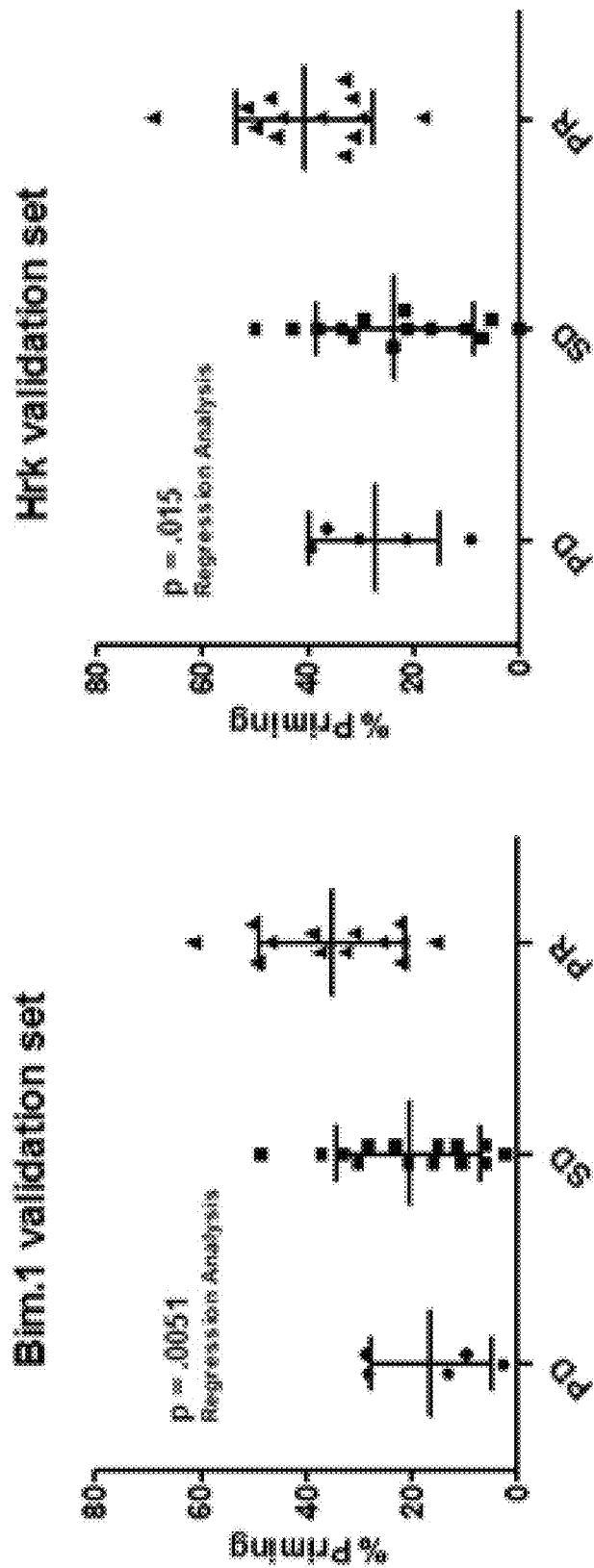
Figure 2C:
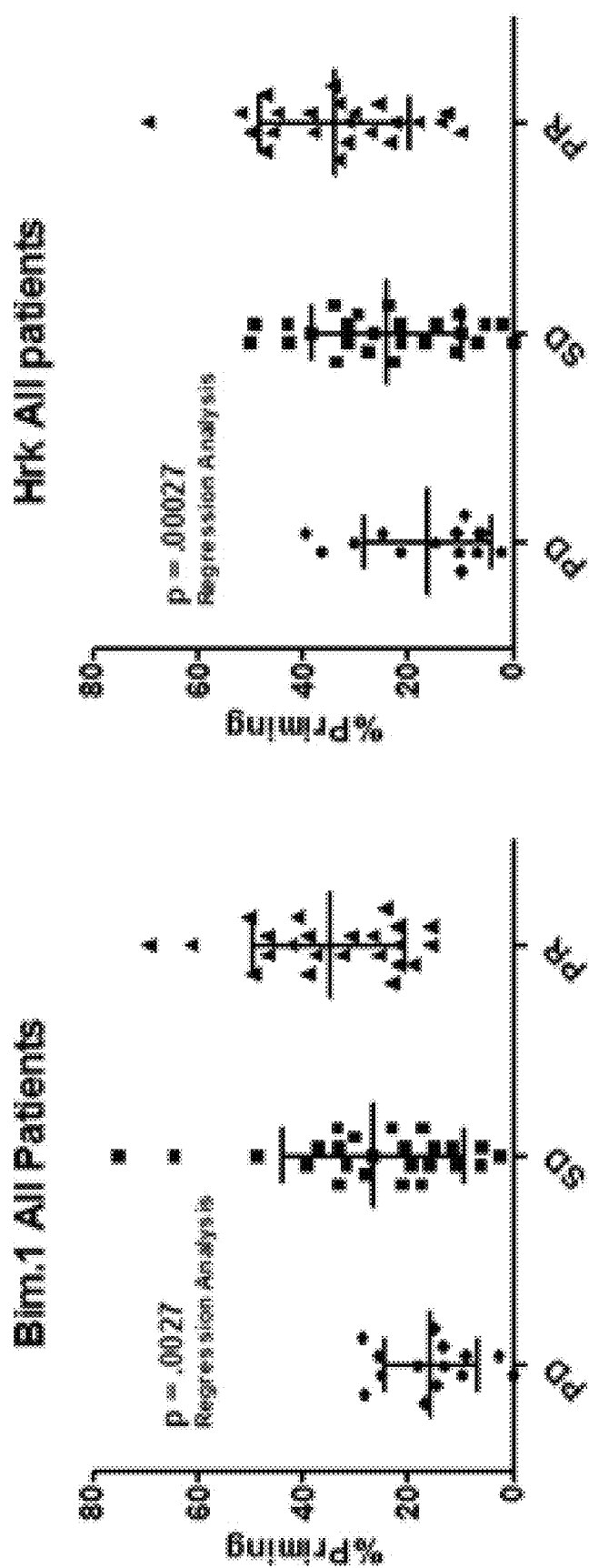

FIG. 2A-C is a series of graphs showing Bim and Hrk BH3 profiling of CLL patients are correlated with alvocidib response in principal and validation cohorts. Dot plot depictions of training and test set cohorts as well as the combined data set by stratification of response into 3 categories (PD, SD, PR).

Figure 3A:
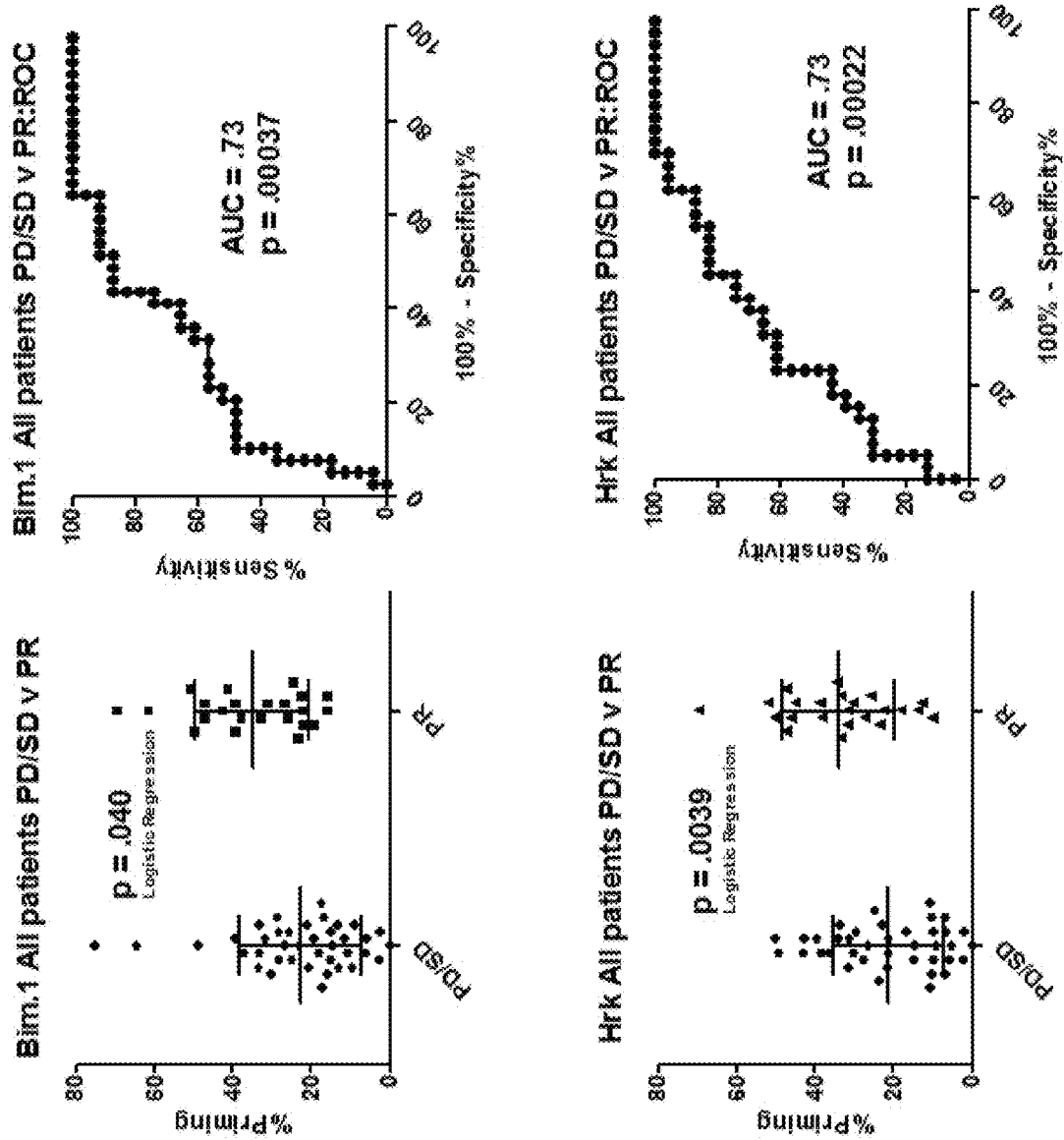
Figure 3B:
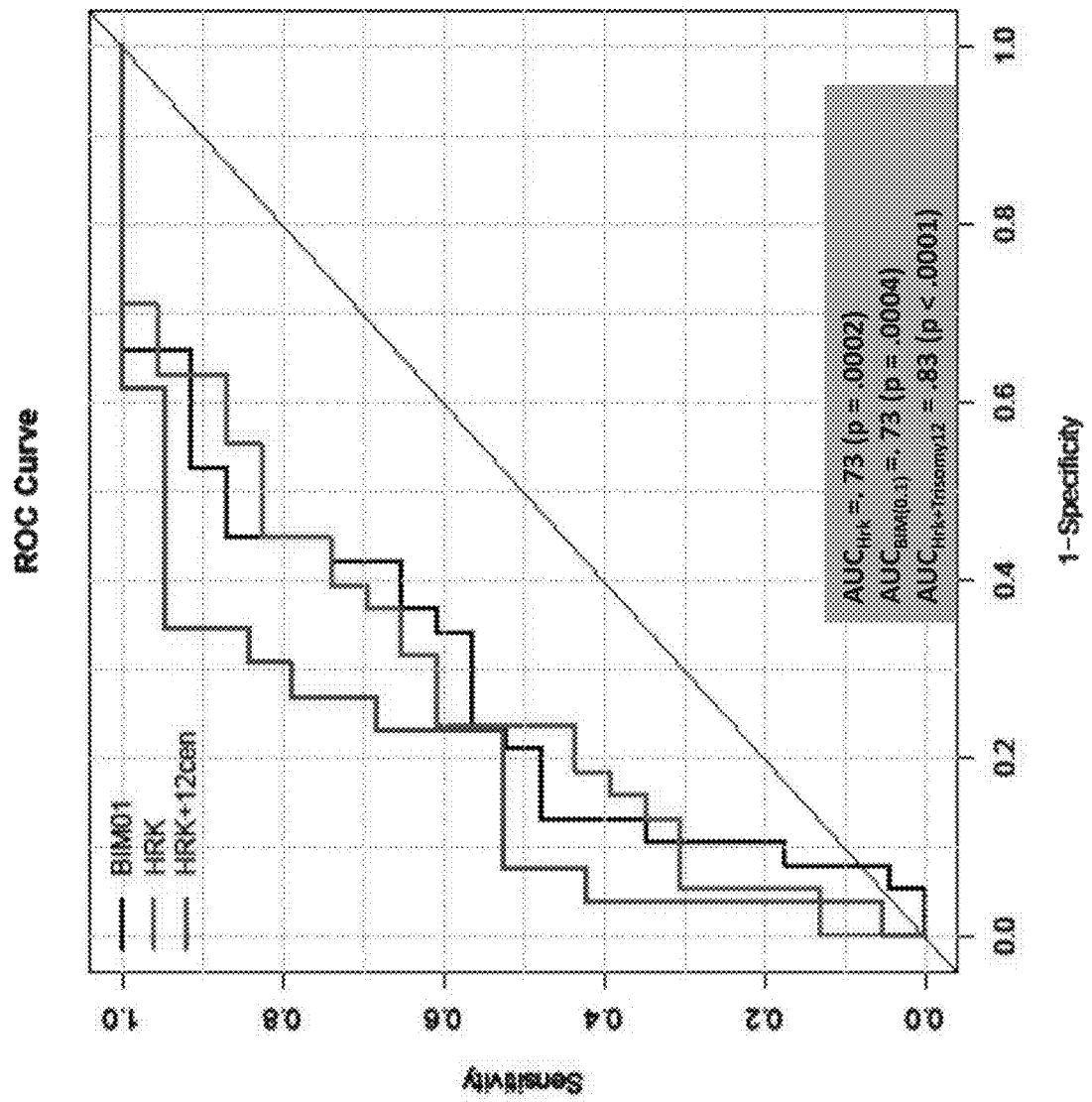

FIG. 3A-B is a series of graphs showing Chromosome 12 trisomy multivariate analysis adds to Hrk prediction of CLL patient clinical response to alvocidib. Dot plot (Panel A) and ROC plot (Panel B) depictions of Bim(0.1) and Hrk response discrimination (2 groups: PD/SD. PR). While both Bim(0.1) and Hrk display AUC from ROC plot depictions of 0.73, Hrk models benefit front inclusion of significant clinical adjustment variable trisomy 12 to yield the increased AUC of 0.83 ($p<0.0001$).

Table 3 shows BH3 profiling biomarkers discriminate patients with Tumor Lysis Syndrome (TLS) to alvocidib treatment. Both BAD and Puma(10) BH3 profiling readouts are predictive of whether a patient may experience TLS following alvocidib treatment. Additionally. ECOG status was significant and age was borderline significant for log regression p-values.

Figure 4A:
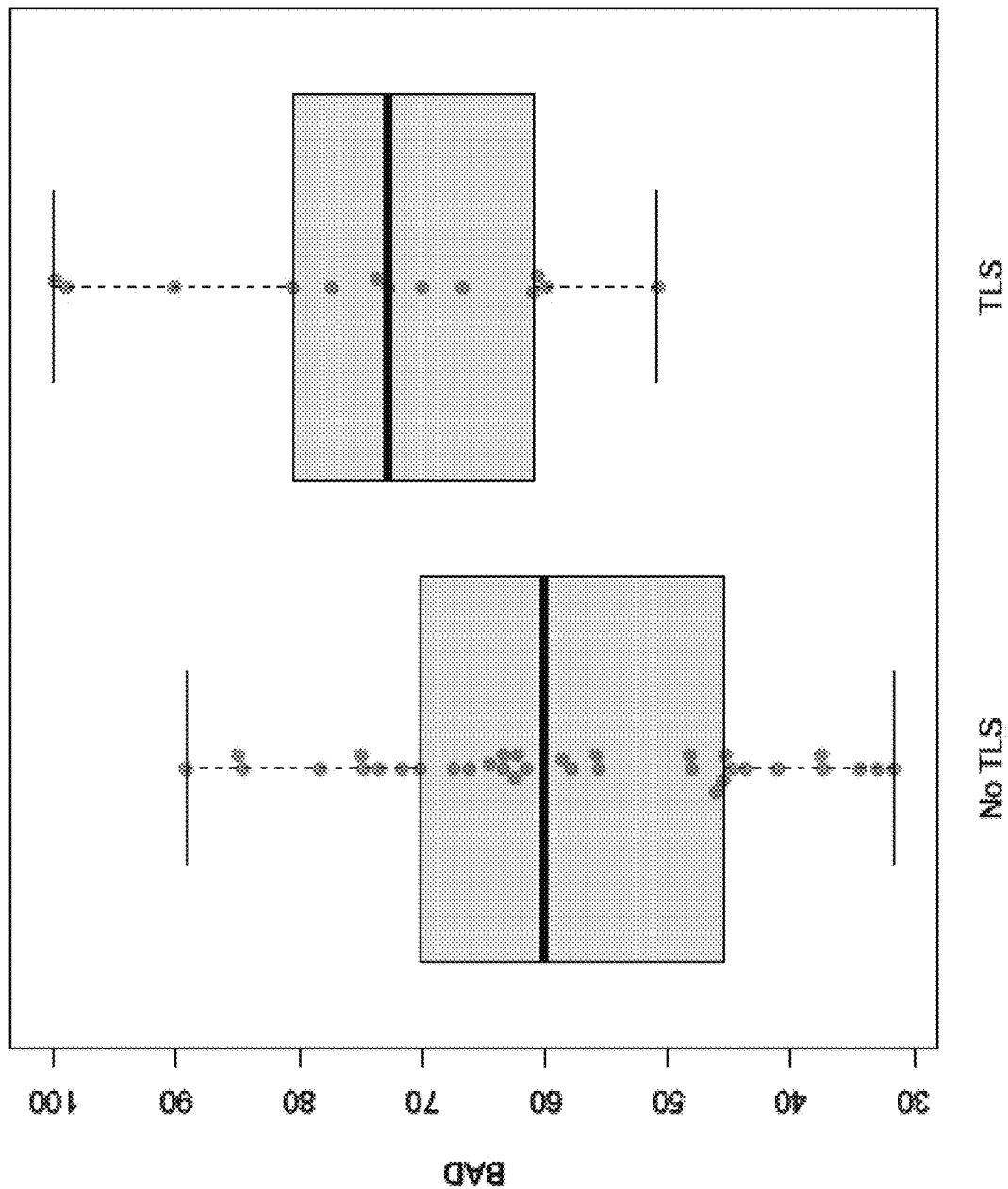
Figure 4B:
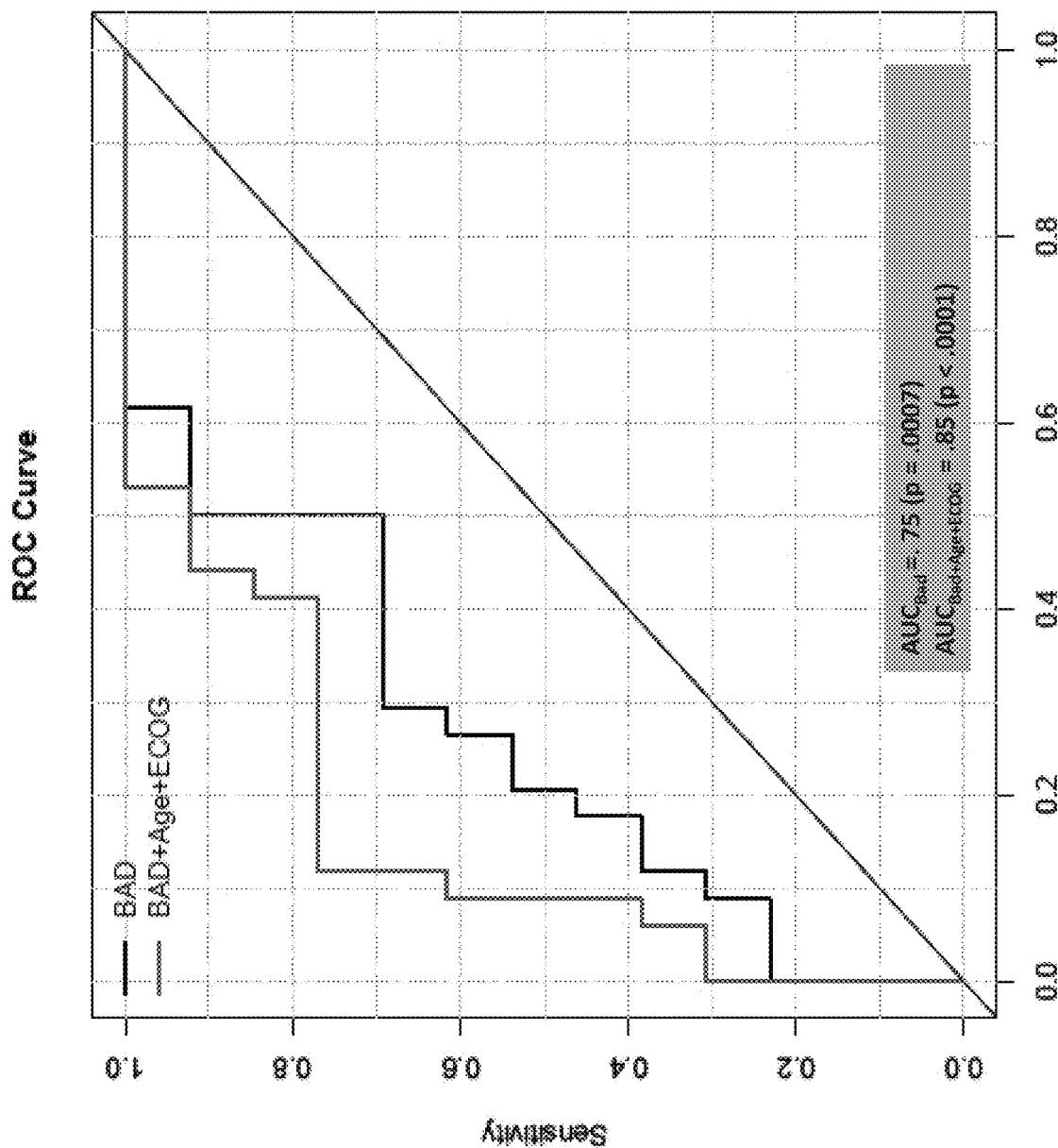

FIG. 4A-B is a series of graphs showing Bad peptide BH3 profiling correlates with ITS in CLL patients following treatment with alvocidib. Dot plot depictions (Panel A) indicate that higher BAD BH3 profiling readout values are significantly associated with the presence of TLS versus those patients who did not experience TLS. The Bad AUC from ROC plot analysis (Panel B) was 0.75; this increased to 0.85 when combined with clinical adjustment variables age and ECOG status.

DETAILED DESCRIPTION OF THE INVENTION

BH3 profiling can provide insight into whether a particular cancer will respond to a selected treatment, in addition to whether that treatment is likely to cause adverse events, such as tumor lysis syndrome (TLS) that hinder the efficacy of treatment. Without being bound by theory, it is thought that cancer cells develop blocks in apoptotic pathways that have the effect of making some cancers resistant to some therapies, and other cancers sensitive to other therapies. The development of these pathway blocks can be determined by BH3 profiling, thereby identifying which cancer cells are susceptible to a particular treatment and which are not. Cancer cells can exhibit abnormalities that would otherwise lead to apoptosis through the intrinsic (mitochondrial) apoptosis pathway, but if this pathway is blocked, the cancer cell will survive.

The Bcl-2 family of proteins, believed to be the key mediator of resistance to chemotherapy in many cancers, are key regulators of mitochondrial outer membrane permeabilization (MOMP), a crucial event that commits a cell to die by apoptosis. Binding among various members of the Bcl-2 family can either activate or sensitize MOMP, depending upon which Bcl-2 proteins bind. By identifying the Bcl-2 protein binding in a cancer cell or specimen, we can determine the apoptotic state of the given cancer (e.g. resistant or sensitive), and whether there is a likelihood of certain adverse events. This information is used to guide the course of treatment.

The present disclosure is based, in part, on the discovery that BH3 profiling (such as implemented in Praedicare Dx™) can predict the likelihood that a patient will experience an adverse response, including tumor lysis syndrome (TLS), upon administration of one or more cancer treatments. Further, the diagnostic approaches described herein are useful in determining the likelihood one or more cancer treatments' efficacy in a patient including, optionally, in combination with a prediction of adverse response.

In one aspect, the present disclosure provides a method for determining an adverse response to one or more cancer treatments in a patient, comprising: determining a BH3 profile for the patient's tumor or cancer cell specimen; and classifying the patient for likelihood of an adverse response to one or more cancer treatments. In some embodiments, the adverse response comprises TLS.

In another aspect, the present disclosure provides a method for determining a treatment response to one or more cancer treatments in a blood cancer patient, comprising: determining a BH3 profile for the patient's tumor or cancer cell specimen; and classifying the patient for likelihood of one or more of an adverse response to one or more cancer treatments and a therapeutic efficacy to one or more cancer treatments wherein a BH3 profile comprising BAD and/or PUMA is indicative of an adverse response to one or more cancer treatments and a BH3 profile comprising BIM and/or HRK is indicative of therapeutic efficacy to one or more cancer treatments.

In other aspects, the cell specimen may be from a patient with, or suspected of having a tumor, but may not be a cell specimen derived from the tumor itself. For example, examples of cells not from the tumor itself include platelets, erythroblast cells, T-helper cell (including TH-1, TH-2, and TH-17), mast cells, macrophages, dendritic cells.

In aspects, the cell specimen may contain an immunomodulating cell. An immunomodulating cell is one that directly or indirectly is involved with infection, tissue repair, tissue self-recognition, tissue homeostasis, inflammation, and cell migration. For example, the immunomodulating cell may be from the total bone marrow or peripheral blood cells.

In some aspects, the diagnostic approaches are as described in PCT/US2013/040585, the contents of which are hereby incorporated by reference in their entirety.

Exemplary Clinical Decisions

In some embodiments, the methods described herein are useful in the evaluation of a patient, for example, for evaluating diagnosis, prognosis, and response to treatment. In various aspects, the present disclosure comprises evaluating a tumor or hematological cancer. In various embodiments, the evaluation may be selected from diagnosis, prognosis, and response to treatment. In various embodiments, the evaluation is a determination of the likelihood of an adverse response. In various embodiments, the evaluation is a determination of therapeutic efficacy.

Diagnosis refers to the process of attempting to determine or identify a possible disease or disorder, such as, for example, cancer. Prognosis refers to predicting a likely outcome of a disease or disorder, such as, for example, cancer. A complete prognosis often includes the expected duration, the function, and a description of the course of the disease, such as progressive decline, intermittent crisis, or sudden, unpredictable crisis. Response to treatment is a prediction of a patient's medical outcome when receiving a treatment. Responses to treatment can be, by way of non-limiting example, pathological complete response, survival, and progression free survival, time to progression, probability of recurrence.

In various embodiments, the present methods direct a clinical decision regarding whether a patient is to receive, or not receive, a specific treatment or therapy. In one embodiment, the treatment or therapy is the primary, main, or initial treatment or therapy. In one embodiment, the present methods are predictive of a positive response to neoadjuvant and/or adjuvant chemotherapy or a non-responsiveness or adverse response to neoadjuvant and/or adjuvant chemotherapy. In one embodiment, the present methods are predictive of a positive response to a pro-apoptotic agent or an agent that operates via apoptosis and/or an agent that does not operate via apoptosis or a non-responsiveness or adverse response to apoptotic effector agent and/or an agent that does not operate via apoptosis. In various embodiments, the present disclosure directs the treatment of a cancer patient, including, for example, what type of treatment should be administered or withheld.

In one embodiment, the present methods direct a clinical decision regarding whether a patient is to receive adjuvant therapy after primary, main or initial treatment, including, without limitation, a single sole adjuvant therapy. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease.

In some embodiments, the present methods direct a patient's treatment to include adjuvant therapy. For example, a patient that is scored to be responsive to a specific treatment may receive such treatment as adjuvant therapy. Further, the present methods may direct the identity of an adjuvant therapy, by way of non-limiting example, as a treatment that induces and/or operates in a pro-apoptotic trimmer or one that does not. In one embodiment, the present methods may indicate that a patient will not be or will be less responsive or will have an adverse response to a specific treatment and therefore such a patient may not receive such treatment as adjuvant therapy. Accordingly, in some embodiments, the present methods provide for providing or withholding adjuvant therapy according to a patient's likely response. In this way, a patient's quality of life, and the cost of care, may be improved.

In various embodiments, the present methods direct a clinical decision regarding whether a patient is to receive neoadjuvant therapy, e.g. therapy to shrink and/or downgrade the tumor prior to surgery. In some embodiments, neoadjuvant therapy means chemotherapy administered to cancer patients prior to surgery. In some embodiments, neoadjuvant therapy means an agent, including those described herein, administered to cancer patients prior to surgery. Types of cancers for which neoadjuvant chemotherapy is commonly considered include, for example, breast, colorectal, ovarian, cervical, bladder, and lung.

In some embodiments, the present methods direct a patient's treatment to include neoadjuvant therapy. For example, a patient that is scored to be responsive to a specific treatment may receive such treatment as neoadjuvant therapy. Further, the present methods may direct the identity of a neoadjuvant therapy, by way of non-limiting example, as a treatment that induces and/or operates in a pro-apoptotic manner or one that does not. In one embodiment, the present methods may indicate that a patient will not be, or will be less responsive, or will have an adverse response to a specific treatment and therefore such a patient may not receive such treatment as neoadjuvant therapy. Accordingly, in some embodiments, the present methods provide for providing or withholding neoadjuvant therapy according, to a patient's likely response. In this way, a patient's quality of life, and the cost of case, may be improved.

In some embodiments, the present methods direct a clinical decision regarding whether a patient is to receive a specific type of treatment. Accordingly, in some embodiments, the present methods are a guiding test for patient treatment.

In some embodiments, the present methods provide information about the likely response that a patient is to have to a particular treatment. In some embodiments, the present methods provide a high likelihood of response and may direct treatment, including aggressive treatment. In some embodiments, the present methods provide a low likelihood of response and may direct cessation of treatment, including aggressive treatment, and the use of palliative care, to avoid unnecessary toxicity from ineffective chemotherapies for a better quality of life. In some embodiments, the present methods provide a high likelihood of an adverse response and may direct cessation of treatment, including aggressive treatment, and the use of palliative care, to avoid unnecessary toxicity from ineffective chemotherapies for a better quality of life. In some embodiments, the present methods provide a low likelihood of an adverse response and m may direct treatment, including, aggressive treatment.

In an exemplary embodiment, the present method will indicate a likelihood of response to a specific treatment. For example, in some embodiments, the present methods indicate a high or low likelihood of response to a pro-apoptotic agent and/or an agent that operates via apoptosis and/or an agent that operates via apoptosis driven by direct protein modulation. In various embodiments, exemplary pro-apoptotic agents and/or agents that operate via apoptosis and/or an agent that operates via apoptosis driven by direct protein modulation include ABT-263 (Navitoclax), and obatoclax, WEP, bortezomib, and carfilzomib. In some embodiments, the present methods indicate a high or low likelihood of response to an agent that does not operate via apoptosis and/or an agent that does not operate via apoptosis driven by direct protein modulation. In various embodiments, exemplary agents that do not operate via apoptosis include kinesin spindle protein inhibitors, cyclin-dependent kinase inhibitor, Arsenic Trioxide (TRISENOX), MEK inhibitors, pomolidomide, azacytidine, decitibine, vorinostat, entinostat, geratuzumab, BTK inhibitors, PI3 kinase delta inhibitors, lenolidimide, anthracyclines, cytarabine, melphalam, Aky inhibitors, mTOR inhibitors.

In an exemplary embodiment, the present method will indicate whether a patient is to receive a pro-apoptotic agent or an agent that operates via apoptosis for cancer treatment. In another exemplary embodiment, the present method will indicate whether a patient is to receive an agent that does not operate via apoptosis.

In a specific embodiment, the present methods are useful in predicting a cancer patient's response and/or likelihood or an adverse reaction to any of the treatments (including agents) described herein. In an exemplary embodiment, the present disclosure predicts an AML patient's likelihood of response to cytarabine and azacytidine and comprises an evaluation of the BH3 profile, age profile and cytogenetic factors of the patient.

In various embodiments, a cancer treatment is administered or withheld based on the methods described herein. Exemplary treatments include surgical resection, radiation therapy (including the use of the compounds as described herein as, or in combination with, radiosensitizing agents), chemotherapy, pharmacodynamic therapy, targeted therapy, immunotherapy, and supportive therapy (e.g., painkillers, diuretics, antidiuretics, antivirals, antibiotics, nutritional supplements, anemia therapeutics, blood clotting therapeutics, bone therapeutics, and psychiatric and psychological therapeutics).

In one embodiment, the methods disclosed herein may be used to classify the patient into a treatment group. In some non-limiting examples, patients are classified into groups designated as responder, non-responder, high likelihood of response, low likelihood of response, high likelihood of adverse response, and low likelihood of adverse response. In further embodiments, patient classification directs a clinical decision regarding treatment, such as, for example, switching from one therapeutic to another, a change in dose of therapeutic, or administration of a different type of treatment (e.g. surgery, radiation, allogenic bone marrow or stem cell transplant). In various embodiments, a cancer treatment is administered or withheld based on the methods described herein.

Exemplary Treatments

In exemplary embodiments, the disclosure selects a treatment agent. Examples of such agents include, but are not limited to, one or more of anti-cancer drugs, chemotherapy, surgery, adjuvant therapy, and neoadjuvant therapy. In one embodiment, the cancer treatment is one or more of a BH3 mimetic, epigenetic modifying agent, topoisomerase inhibitor, cyclin-dependent kinase inhibitor, and kinesin-spindle protein stabilizing agent. In another embodiment, the cancer treatment is a proteasome inhibitor; and/or a modulator of cell cycle regulation (by way of non-limiting example, a cyclin dependent kinase inhibitor); and/or a modulator of cellular epigenetic mechanistic (by way of non-limiting example, one or more of a histone deacetylase (HDAC) (e.g. one or more of vorinostat or entinostat), azacytidine, decitabine); and/or an anthracycline or anthracenedione way of non-limiting example, one or more of epirubicin, doxorubicin, mitoxantrone, daunorubicin, idarubicin); and/or a platinum-based therapeutic (by way of non-limiting example, one or more of carboplatin, cisplatin, and oxaliplatin); cytarabine or a cytarabine-based chemotherapy; a BH3 mimetic (by way of non-limiting example, one or more of BCL2, BCLXL, or MCL1); and an inhibitor of MCL1.

In various embodiments, the disclosure pertains to cancer treatments including, without limitation, those described in U.S. Patent Publication No. US 2012-0225851 and International Patent Publication No. WO 2012/122370, the contents of which are hereby incorporated by reference in their entireties.

In various embodiments, the disclosure pertains to cancer treatments including, without limitation, one or more of alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norlencine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodonibicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as aneitabine, azacitidine, 6-azauridine, camiofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid, gallium nitrate; hydroxy urea; lentinan; lonidainine; maytansinoids such as may tansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; filizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil, GEMZAR gemcitabine; 6-thioguanine; mercaptopurine; methotrexate; platinum analogs such as cisplatin, oxaliplatin and carboplatin; vinblastine; platinum, etoposide (VP-16); ifosfamide; mitoxantrone; vincristine; NAVELBINE, vinorelbine; novantrone; teniposide; edatrexate, datmomycin, aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation, dacogen, velcade, and pharmaceutically acceptable salts, acids or derivatives of any of the above.

Exemplary Detection Methods

In various embodiments, the present methods comprise evaluating a presence, absence, or level of a protein and/or a nucleic acid. In various embodiments, the present methods comprise evaluating a presence, absence, or level of a protein and/or a nucleic acid which can enhance the specificity and/or sensitivity of BH3 profiling. In some embodiments, the evaluating is of a marker for patient response. In some embodiments, the present methods comprise measurement using one or more of immunohistochemical staining, western blotting, in cell western, immunofluorescent staining, ELISA, and fluorescent activating cell sorting (FACS), or any other method described herein or known in the art.

The present methods may comprise contacting an antibody with a tumor specimen (e.g. biopsy or tissue or body fluid) to identify an epitope that is specific to the tissue or body fluid and that is indicative of a state of a cancer.

There are generally two strategies used for detection of epitopes on antigens in body fluids or tissues, direct methods and indirect methods. The direct method comprises a one-step staining, and may involve a labeled antibody (e.g. FTC conjugated antiserum) reacting directly with the antigen in a body fluid or tissue sample. The indirect method comprises an unlabeled primary antibody that reacts with the body fluid or tissue antigen, and a labeled secondary antibody that reacts with the primary antibody. Labels can include radioactive labels, fluorescent labels, hapten labels such as, biotin, or an enzyme such as horse radish peroxidase or alkaline phosphatase. Methods of conducting these assays are well known in the art. See, e.g., Harlow et al. (Antibodies, Cold Spring Harbor Laboratory, N.Y., 1988), Harlow et al. (Using Antibodies, A Laboratory Manual, Cold Spring Harbor Laboratory, N.Y., 1999), Virella (Medical Immunology, 6th edition. Informa HealthCare, New York, 2007), and Diamandis et al. (Immunoassays, Academic Press. Inc., New York, 1996). Kits for conducting these assays are commercially available from, for example, Clontech Laboratories, LLC. (Mountain View, Calif.).

In various embodiments, antibodies include whole antibodies and/or any antigen binding fragment (e.g., an antigen-binding portion) and/or single chains of these (e.g. an antibody comprising at least two heavy (H) chains and two light (L) chains inter-connected by disulfide bonds, an Fab fragment, a monovalent fragment consisting of the $V_L$, $V_H$, $C_L$ and CH1 domains; a F(ab)$_2$ fragment, a bivalent fragment including two Fab fragments linked by a disulfide bridge at the hinge region; a Fd fragment consisting of the $V_H$ and CH1 domains; a Fv fragment consisting of the $V_L$ and $V_H$ domains of a single arm of an antibody; and the like). In various embodiments, polyclonal and monoclonal antibodies are useful, as are isolated human or humanized antibodies, or functional fragments thereof.

Standard assays to evaluate the binding ability of the antibodies toward the target of various species are known in the art, including for example, ELISAs, western blots and RIAs. The binding kinetics (e.g., binding affinity) of antibodies also can be assessed by standard assays known in the art, such as by Biacore analysis.

In another embodiment, the measurement comprises evaluating a presence, absence, or level of a nucleic acid. A person skilled in the art will appreciate that a number of methods can be used to detect or quantify the DNA/RNA levels of appropriate markers.

Gene expression can be measured using, for example, low-to-mid-plex techniques, including but not limited to reporter gene assays. Northern blot, fluorescent in situ hybridization (FISH), and reverse transcription PCR (RT-PCR). Gene expression can also be measured using, for example, higher-plex techniques, including but not limited, serial analysis of gene expression (SAGE), DNA microarrays. Tiling array, RNA-Seq/whole transcriptome shotgun sequencing (WTSS), high-throughput sequencing, multiplex PCR, multiplex ligation-dependent probe amplification (MLPA), DNA sequencing by ligation, and Luminex/XMAP. A person skilled in the art will appreciate that a number of methods can be used to detect or quantify the level of RNA products of the biomarkers within a sample, including arrays, such as microarrays, RT-PCR (including quantitative PCR), nuclease protection assays and Northern blot analyses.

Exemplary Cancers and Patients

In some embodiments the disclosure provides a method for determining a cancer treatment and/or comprises a patient's tumor or cancer cell specimen. A cancer or tumor refers to an uncontrolled growth of cells and/or abnormal increased cell survival and/or inhibition of apoptosis which interferes with the normal functioning of the bodily organs and systems. A subject that has a cancer or a tumor is a subject having objectively measurable cancer cells present in the subject's body. Included in this disclosure are benign and malignant cancers, as well as dormant tumors or micro-metastases. Cancers which migrate from their original location and seed vital organs can eventually lead to the death of the subject through the functional deterioration of the affected organs.

In various embodiments, the disclosure is applicable to pre-metastatic cancer, or metastatic cancer. Metastasis refers to the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are often detected through the sole or combined use of magnetic resonance imaging (MRI) scans, computed tomography (CT) scans, blood and platelet counts, liver function studies, chest X-rays and bone scans in addition to the monitoring of specific symptoms.

The methods described herein are directed toward the prognosis of cancer, diagnosis of cancer, treatment of cancer, and/or the diagnosis, prognosis, treatment, prevention or amelioration of growth, progression, and/or metastases of malignancies and proliferative disorders associated with increased cell survival, or the inhibition of apoptosis. In some embodiments, the cancer is a hematologic cancer, including, but not limited to, acute myelogenous leukemia (AML), multiple myeloma, follicular lymphoma, acute lymphoblastic leukemia (ALL), chronic lymphocytic leukemia, and non-Hodgkin's lymphoma including, but not limited to, mantle cell lymphoma and diffuse large B-cell lymphoma. In some embodiments, the cancer is a solid tumor, including, but not limited to, non-small lung cell carcinoma, ovarian cancer, and melanoma.

In some embodiments, the disclosure relates to one or more of the following cancers: acute lymphoblastic leukemia (ALL), acute myeloid leukemia (AML), adrenocortical carcinoma, AIDS-related cancers, anal cancer, appendix cancer, astrocytoma (e.g. childhood cerebellar or cerebral), basal-cell carcinoma, bile duct cancer, bladder cancer, bone tumor (e.g. osteosarcoma, malignant fibrous histiocytoma), brainstem glioma, brain cancer, brain tumors (e.g. cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomaslcarcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous t-cell lymphoma, desmoplastic small round cell tumor, endomettial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g. extracranial, extragonadal, ovarian), gestational trophoblastic tumor, gliomas (e.g. brain stem, cerebral astrocytom, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g. acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g. non-small cell, small cell), lymphoma (e.g. AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, phalyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primly central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g. Ewing family, Kaposi, soft tissue, uterine), Sézary syndrome, skin cancer (e.g. nonmelanoma, melanoma, merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenström macroglobulinemia, and Wilms tumor.

In one embodiment, the cancer is AML. AML is the second most common leukemia, with approximately 13,000 newly diagnosed cases and 9,000 deaths annually in the US. Although approved therapies exist, the prognosis of many leukemia patients is poor and the likelihood of successful treatment is low. The current standard of care for AML is induction cytosine arabinoside (ara-C) in combination with an anthracycline agent (such as, for example, daunarubicin, idarubicine or mitoxantrone). This therapeutic regimen is typically followed by administration of high dose cytarabine and/or stem cell transplantation. These treatments have improved outcome in young patients. Progress has also been made in the treatment of acute promyelocytic leukemia, where targeted therapy with all-trans retinoic acid (ATRA) or arsenic trioxide have resulted in excellent survival rates. However, patients over 60, a population which represents the vast majority of AML cases, remain a therapeutic enigma. Although 65-85% of patients initially respond to existing treatments, 65% of such responders undergo relapse, and many patients succumb to the disease. For at least this reason and because the afore-mentioned treatments may have severe side effects, the inventive predictive test can guide use of the treatment that mitigates these litigations. In some embodiments, the present disclosure improves the likelihood of successful treatment by matching the right patient to the right treatment. Further, there are currently no tests to predict AML patient response to treatment.

The term subject, as used herein unless otherwise defined, is a mammal, e.g., a human, mouse, rat, hamster, guinea pig, dog, cat, horse, cow, goat, sheep, pig, or non-human primate, such as a monkey, chimpanzee, or baboon. The terms "subject" and "patient" are used interchangeably.

Exemplary Specimens

In some embodiments, the present disclosure includes the measurement of a tumor specimen, including biopsy or surgical specimen samples. In some embodiments, the specimen is selected from a frozen tumor tissue specimen, cultured cells, circulating tumor cells, and a formalin-mixed paraffin-embedded tumor tissue specimen (e.g. for antibody based BH3 profiling). In some embodiments, the biopsy is a human biopsy. In various embodiments, the biopsy is any one of a frozen tumor tissue specimen, cultured cells, circulating tumor cells, and a formalin-fixed paraffin-embedded tumor tissue specimen (e.g. for antibody based BH3 profiling).

In some embodiments, the tumor specimen may be a biopsy sample, such as a frozen tumor tissue (cryosection) specimen. As is known in the art, a cryosection may employ a cryostat, which comprises a microtome inside a freezer. The surgical specimen is placed on a metal tissue disc which is then secured in a chuck and frozen rapidly to about −20° C. to about −30° C. The specimen is embedded in a gel like medium consisting of, for example, poly ethylene glycol and polyvinyl alcohol. The frozen tissue is cut frozen with the microtome portion of the cryostat, and the section is optionally picked up on a glass slide and stained.

In some embodiments, the tumor specimen may be a biopsy sample, such as cultured cells. These cells may be processed using the usual cell culture techniques that are known in the art. These cells may be circulating tumor cells.

In some embodiments, the tumor specimen may be a biopsy sample, such as a formalin-fixed paraffin-embedded (FFPE) tumor tissue specimen. As is known in the art, a biopsy specimen may be placed in a container with formalin (a mixture of water and formaldehyde) or some other fluid to preserve it. The tissue sample may be placed into a mold with hot paraffin wax. The wax cools to form a solid block that protects the tissue. This paraffin wax block with the embedded tissue is placed on a microtome, which cuts very thin slices of the tissue.

In certain embodiments, the tumor specimen (or biopsy) contains less than 100 mg of tissue, or in certain embodiments, contains about 50 mg of tissue or less. The tumor specimen (or biopsy) may contain from about 20 mg to about 50 mg of tissue, such as about 35 mg of tissue.

The tissue may be obtained, for example, as one or more (e.g., 1, 2, 3, 4, or 5) needle biopsies (e.g., using a 14-gauge needle or other suitable size). In some embodiments, the biopsy is a fine-needle aspiration in which a long, thin needle is inserted into a suspicious area and a syringe is used to draw out fluid and cells for analysis. In some embodiments, the biopsy is a core needle biopsy in which a large needle with a cutting tip is used during core needle biopsy to draw a column of tissue out of a suspicious area. In some embodiments, the biopsy is a vacuum-assisted biopsy in which a suction device increases the amount of fluid and cells that is extracted through the needle. In some embodiments, the biopsy is an image-guided biopsy in which a needle biopsy is combined with an imaging procedure, such as, for example, X ray, computerized tomography (CT), magnetic resonance imaging (MRI) or ultrasound. In other embodiments, the sample may be obtained via a device such as the MAMMOTOME® biopsy system, which is a laser guided, vacuum-assisted biopsy system for breast biopsy.

In certain embodiments, the specimen is a human tumor-derived cell line. In certain embodiments, the specimen is a cancer stem cell. In other embodiments, the specimen is derived from the biopsy of a solid tumor, such as, for example, a biopsy of a colorectal, breast, prostate, lung, pancreatic, renal, or ovarian primary tumor.

In certain embodiments, the specimen is of epithelial origin. In some embodiments, the epithelial specimen is enriched by selection from a biopsy sample with an anti-epithelial cell adhesion molecule (EpCAM) or other epithelial cell binding antibody bound to solid matrix or bead.

In certain embodiments, the specimen is of mesenchymal origin. In some embodiments, the mesenchymal specimen is enriched by selection from a biopsy sample with a neural cell adhesion molecule (N-CAM) or neuropitin or other mesenchymal cell binding antibody bound to a solid matrix or bead.

In certain embodiments, the specimen is derived from the biopsy of a non-solid tumor, such as, for example, any of the cancer described herein. In specific embodiments, the specimen is derived from the biopsy of a patient with multiple myeloma, acute myelogenous leukemia, acute lymphocytic leukemia, chronic lymphogenous leukemia mantle cell lymphoma, diffuse large B-cell lymphoma, and non-Hodgkin's lymphoma. In a specific embodiment, the specimen is a multiple myeloma cell that is enriched by selection from a biopsy sample with an anti-CD138 antibody hound to a solid matrix or bead. In a specific embodiment, the specimen is an acute myelogenous leukemia cell that is enriched by binding to a CD45-directed antibody. In a specific embodiment, the specimen is a chronic lymphogenous leukemia or diffuse large B-cell lymphoma that is enriched by non-B cell depletion.

in some embodiments, the specimen is derived from a circulating tumor cell. In some embodiments, the specimen is derived from a circulating tumor cell. In some embodiments, the specimen is performed on purified B cells from a cancer patient.

BH3 Profiling

In various embodiments, the disclosure comprises BH3 profiling. In various embodiments, the disclosure comprises BH3 profiling in which at least two, or three, or four, or five, or six, or seven, or eight, or nine, or ten BH3 peptides are evaluated at once. In some embodiments, the present methods comprise a multipeptide analysis, as opposed to an evaluation of a single BH3 peptide. In some embodiments, a panel of BH3 peptides is screened on a single patient specimen.

In some embodiments, the BH3 profiling comprises use of a peptide, wherein the peptide is one or more of BIM, BIM2A, BAD, BID, HRK, PUMA, NOXA, BMF, BIK, and PUMA2A. In some embodiments, the BH3 profiling comprises use of an antibody directed against one of more of BIM, BIM2A, BAD, BID, HRK, PUMA, NOXA, BMF, BIK, and PUMA2A and naturally-occurring heterodimers formed between two Bcl-2 proteins, e.g. a first Bcl-2 protein (e.g., Bim, Bid, Bad, Puma, Noxa, Bak, Hrk, Bax, or Mule) and a second Bcl-2 protein (e.g., Mcl-1, Bcl-2, Bcl-XL, Bfl-1 or Bcl-w) as described in U.S. Pat. No. 8,168,755, the contents of which are hereby incorporated by reference in their entireties. In some embodiments the BH3 profiling comprises use of a stapled peptide (e.g. a peptide generated through the synthetic enhancement of a 3-D alpha-helix protein segment with hydrocarbon bonds to make proteins more rigid and able to penetrate cells), as described in, for example, Verdine, et al. "Stapled Peptides for intracellular Drug Targets" Methods in Enzymology, Volume 503 (Chap. 1), the contents of which are hereby incorporated by reference in their entireties.

In one embodiment, the peptide is used at a concentration of about 0.1 to about 200 µM. In some embodiments, about 0.1 to about 150, or about 0.1 to about 100, or about 0.1 to about 50, or about 0.1 to about 10, or about 0.1 to about 5, about 1 to about 150, or about 1 to about 100, about 1 to about 50, about 1 to about 10, about 1 to about 5 µM, or about 10 to about 100 µM of the peptide is used. In some embodiments, a concentration of about 0.1, or about 0.5, or about 1.0, or about 5, or about 10, or about 50, or about 100, or about 150, or about 200 µM of the peptide is used. In one embodiment, the BH3 profiling comprises permeabilizing a specimen.

BH3 profiling and reagents useful for such a method is described in U.S. Pat. Nos. 7,868,133; 8,221,966; and 8,168,755 and U.S. Patent Publication No. 2011/0130309, the contents of which are hereby incorporated by reference in their entireties.

Briefly, without wishing to be bound by theory, as a result of aberrant phenotypes, cancer cells develop blocks in apoptosis pathways. These blocks make cancer cells both resistant to some therapies, and, surprisingly, make some cancer cells sensitive to other therapies. The concept of "oncogene addiction" describes the phenomena of the acquired dependence of cancer cells on, or addiction to, particular proteins for survival. BH3 profiling determines if such a dependence on certain apoptosis regulating proteins occurs in given cancer cells, and identifies the dependent protein. Cancer cells can be, but are not always, pre-set to undergo apoptosis and this is a function of these cells being dependent on any, or all of the anti-apoptotic Bcl-2 family proteins for their otherwise unintended survival. This provides insight into the likelihood of a cancer cell to respond to treatment.

Cancer cells, without wishing to be bound by theory, exhibit abnormalities, such as DNA damage, genetic instability, abnormal growth factor signaling, and abnormal or missing, matrix interactions, any of which should typically induce apoptosis through the intrinsic (mitochondrial) apoptosis pathway. However, rather than respond to these apoptosis signals cancer cells survive. Often, in doing so, these cells become highly dependent on selected blocks to chronic apoptosis signals. This adaptation provides a survival mechanism for the cancer cells; however, these adaptations can also make cancer cells susceptible to particular apoptosis inducing therapies. A crucial event that commits a cell to die by intrinsic apoptosis is the permeabilization of the mitochondrial outer membrane (MOMP) and the release of molecules that activate the effector caspases. In many cases, MOMP is the point of no return in the intrinsic apoptosis pathway. The Bcl-2 family proteins are the key regulators of MOMP, and their activity is linked to the onset of lymphoid and several solid tumor cancers and is believed in many cancers to be the key mediator of resistance to chemotherapy.

Bcl-2 proteins are regulated by distinct protein-protein interactions between pro-survival (anti-apoptotic) and pro-apoptotic members. These interactions occur primarily through BED (Bcl-2 homology domain-3) mediated binding. Apoptosis-initiating signaling occurs for the most part upstream of the mitochondria and causes the translocation of short, BH3-only, Bcl-2 family members to the mitochondria where they either activate or sensitize MOMP. The activator BH3 only proteins. Bim and Bid, bind to and directly activate the effector, pro-apoptotic proteins Bax and Bak, and also bind to and inhibit the anti-apoptotic Bcl-2 family proteins, Bcl-2, Mcl-1, Bfl-1, Mcl-w and Bcl-xL. The sensitizer BH3 proteins, Bad, Bik, Noxa, Hrk, Bmf and Puma, bind only to the anti-apoptotic Bcl-2 family proteins, Bcl-2, Mcl-1, Bfl-1, Bcl-w and Bcl-xL, blocking their anti-apoptotic functions. Without wishing to be bound by theory, each sensitizer protein has a unique specificity profile. For example, Noxa (A and B) bind with high affinity to Mcl-1, Bad binds to Bcl-xL and Bcl-2 but only weakly to Mcl-1, and Puma binds well to all three targets. An anti-apoptotic function of these proteins is the sequestering of the activator BH3 protein Bim and Bid. Displacement of these activators by sensitizer peptides results in Bax/Bak-mediated apoptotic commitment. These interactions can have various outcomes, including, without limitation, homeostasis, cell death, sensitization to apoptosis, and blockade of apoptosis.

A defining feature of cancer cells in which apoptotic signaling is blocked is an accumulation of the BH3 only activator proteins at the mitochondrial surface, a result of these proteins being sequestered by the anti-apoptotic proteins. This accumulation and proximity to their effector target proteins accounts for increased sensitivity to antagonism of Bcl-2 family proteins in the "BH3 primed" state.

In some embodiments, a cell yielding a high apoptotic response to Noxa (A or B) is Mcl-1 primed, while a high response to the peptide Bad indicates that Bcl-xL or Bcl-2 provides the apoptotic block. In some embodiments, Puma reflects pan-Bcl-2 family priming. In this way, cells that are dependent on either Mcl-1, or Bcl-xL, on both proteins, or on several Bcl-2 family members are readily distinguished so that appropriate treatment may be tailored accordingly. The distinctions in mitochondrial response to these peptides guides the use of therapies that are known to work through pathways that funnel into either Mcl-1 or Bcl-xL affected intrinsic signaling. The use of a Bcl-2 inhibiting or a Mcl-1 inhibiting compound may be indicated in such cases. In some embodiments, the present methods also indicate or contraindicate therapies that target entities upstream of Mcl-1 or Bcl-xL.

BH3 profiling assay identifies when a cell is in the primed state, as well as in which configuration the priming has occurred. The state of the cell can be used to predict adverse events and/or therapeutic efficacy of one or more cancer treatments.

Adverse Events

Adverse events (AEs) arise during cancer therapy and are associated with poor outcomes. For example, hematologic adverse events (AEs) are commonly encountered in patients with (multiple myeloma) MM, AML, CLL and other hematological cancers owing to the nature of the disease and the effects of existing, treatments.

The hematologic complications in patients with MM include, but is not limited to, anemia and may be attributable to chronic, bleeding, or hemolysis, as well as relative deficiency of erythropoietin. Examples, of other hematologic comorbidities commonly found in patients with MM are thrombocytopenia and neutropenia. During the course of the disease, the majority of patients will experience some degree in both cellular and humoral immunity suppression, secondary to T-cell dysfunction, hypogammaglobulinemia, and granulocytopenia.

These hematologic complications in MM are often further exacerbated by current therapeutic regimens, which often include an immunomodulatory drug (IMiD), such as thalidomide and the thalidomide analogs lenalidomide, and porrolidomide, or a proteasome inhibitor (PI), such as bortezomib or carfilzomib.

Identifying patients who are at risk of treatment-caused adverse events enables the physician to take preventative steps. For example, in a patient identified as at-risk for anemia, treatment with erythropoietin may be warranted. Early identification of patient risk of AEs thus allows advanced treatment could prevent drug induced comorbidities.

The BH3 profiling assays disclosed herein may be applied to a variety of adverse events (AE) to guide a therapeutic regimen. By using algorithm readouts from the BH3 profiling assays patients at risk for a variety of adverse events can be identified.

Suitable AEs for analysis using BH3 profiling assay include, but are not limited to: Leukocytosis-high WBC counts; Leukopenia-low WBC counts; Pan-cytosis-all blood cell types are low; Pan-cytopenia-all blood cell types are low; Thrombocytosis-high platelet counts; Thrombocytopenia-low platelet counts; Polycythemia-high RBC counts; Anemia-low RBC counts; Lymphocytosis-high lymphocyte counts; Lymphopenia-low lymphocyte counts; Myelocytosis-high myeloid counts; and Myelopenia-low myeloid counts.

In particular aspects, the AEs listed above may be recognized by algorithms performed on data obtained from BH3 profiling assays run on the pre-treatment samples or specimen from MM, AML, CLL patients who have been diagnosed. In other aspects, related algorithms may be applied to other hematological cancers including ALL, NHL, DLBCL, MDS, or FL.

We have established a method for converting BH3 profiling readouts of the existing native state of Bcl-2 proteins in cancer cells into a context for clinical determinations. The clinical correlation studies were initially intended to identify patients most likely to have a positive response to treatment. To do this assay readouts are applied to response. Patients are categorized as non-responder, partial responder, or responder. We have now discovered that BH3 profiling readouts can be applied to identify individuals that will have adverse events (AEs).

The method for assessing likelihood of drug induced adverse events using BH3 profiling readouts comprises, or in some cases, consists of the following steps: Collecting diagnosed patient samples (e.g. peripheral blood or bone marrow biopsied specimens); Performing Praedieare Dx™ test comprising BH3 profiling as described; Identifying mitochondrial membrane potential shifts in response to peptide, combinations of peptides, combinations of peptides and small molecule BH3 mimetics, or small molecule mimetics alone; Matching those readouts to the occurrence to one or more Adverse Events in patients to develop an algorithm; Combining the results of the algorithm with other clinical prognostic markers to determine a clinical outcome.

Tumor Lysis Syndrome (TLS)

In particular aspects, the adverse event may be Tumor Lysis Syndrome. Tumor lysis syndrome (TLS) is a group of metabolic complications that can occur after treatment of cancer, for example, lymphomas and leukemias, and sometimes even without treatment. These complications are caused by the breakdown products of dying cancer cells, and include hyperkalemia, hyperphosphatemia, hyperuricemia and hyperuricosuria, hypocalcemia, and consequent acute uric acid nephropathy and acute renal failure.

The most common tumors associated with TLS are poorly differentiated lymphomas, such as Burkitt's lymphoma, and leukemias, such as acute lymphoblastic leukemia (ALL) and acute myeloid leukemia (AML). Other cancers (such as melanoma) have also been associated with TLS but are less common.

Usually, the precipitating medication regimen includes combination chemotherapy, but TLS can be triggered in cancer patients by steroid treatment alone, and sometimes without any treatment in this case the condition is referred to as "spontaneous tumor lysis syndrome."

Symptoms and pathogenesis include, for example, hyperkalemia, hyperphosphatemia, hyperphosphatemia, hypocalcemia, hypertiricemia lactic acidosis, and pretreatment spontaneous tumor lysis syndrome.

TLS should be suspected in patients with large tumor burden who develop acute renal failure along with hyperuricemia (e.g. >about 15 mg/dL) or hyperphosphatemia (e.g. >about 8 g/dL)

In some embodiments, the Cairo-Bishop definition of TLS is employed. The Cairo-Bishop definition of laboratory tumor lysis syndrome includes an abnormality in two or more of the following, occurring within three days before or seven days after chemotherapy: uric acid>about 8 mg/dL or about 25% increase; potassium about 6 meq/L or about 25% increase; phosphate>about 4.5 mg/dL or about 25% increase; and calcium<about 7 mg/dL or about 25% decrease. The Cairo-Bishop definition of laboratory tumor lysis syndrome includes laboratory tumor lysis syndrome plus one or more of the following: increased serum creatinine (about 1.5 times upper limit of normal); cardiac arrhythmia or sudden death; and seizure. A grading scale (0-5) is used depending on the presence of lab TLS, serum creatinine, arrhythmias, or seizures.

In some embodiments, the present methods are predictive of TLS in a patient upon administration of one or more cancer treatments. In some embodiments, a high likelihood of TLS directs a withholding of the cancer treatment likely to cause such an adverse response. In some embodiments, a high likelihood of TLS directs treatment to prevent the onset of TLS, including, for example, a xanthine oxidase inhibitor (e.g. allopurinol) and/or a urate oxidase enzyme (e.g. rasburicase (uricase)).

To determine variables from the BH3 profiling assay associated with Tumor lysis syndrome: BH3 profiling is performed on patient samples collected prior to treatment (e.g. with alvocidib); Analysis is performed comparing the single variable, BH3 peptides alone or with other clinical variables including but not limited to, cytogenetic status, age, and gender, for instance, to the occurrence of tumor lysis syndrome; and significance is established using statistical methodologies including, Wilcox p-value, Log regression p-value and AUC p-value For example, as shown in FIG. 4, in CLL patients who were treated with alvocidib priming with BAD was significantly associated with the presence of MS versus patients who did not experience TI-S. The AUC from ROC-plot analysis for BAD was 0.75; this increased to 0.85 when combined with clinical adjustment variables age and ECOG status.

The occurrence of tumor lysis syndrome in CLL patients enrolled in the study of the Abbott drug ABT-263, Navitoclax, caused the halt of the study and the failure of the drug. It is likely that the failure of the drug would have been avoided if there had been a way to identify those patients who arc highly likely to encounter the adverse events. Knowing susceptible patients allows guidance of the drug use and changes in treatment to be determined.

Predicting Adverse Effects Pre-Treatment Patients

Negative reactions to pharmacologic agents are due to multiple risk factors. Combining BH3 priming readouts with other determinants in algorithm readouts provide prognostic and predictive correlates to the development of multiple types of adverse events that result from treatment with chemotherapeutic therapies.

The contribution of BH3 priming to these events, specific adverse events, along with other risk factors including age, cytogenetic status, etc. is determined using multivariate analysis. When significant associations between priming states (and other risk factors) and occurrence of side effects are identified, individual algorithms are developed to determine the likelihood of those side effects as a result of the agents. These algorithms are identified in test cases, and the exact contribution of each risk factor to a probability score for side effects is determined empirically. Each algorithm may be validated on larger groups of patient samples. By applying the algorithm a report is generated that summarizes the likelihood of response to treatments as well as the chance of development of specific adverse events. The data may be used to tailor the treatment regimen to address these concerns.

Hypothetical Algorithms, A, B and C are constant:

Probability Score$_{Drug\ A\ Response}$=$A$×[BIM Priming (tumor cells)]+$B$+[Age]−$C$×[Cytogenetic Risk Score]

Probability Score$_{Drug\ A\ Anemia}$=$A$×[HRK Priming (erythroblast cells)−Noxa Priming (erythroblast cells)]+$B$+[Age]+$C$×[RBC Count]

Probability Score$_{Drug\ A\ Tumor\ Lysis}$=$A$[BAD Priming (tumor cells)]−$B$×[Cytogenetic Risk Score]+$C$×[% BoneMarrow Blasts]

Probability Score$_{Drug\ A\ Tumor\ Lysis}$=$A$[BAD Priming (Macrophage)−PUMA priming(Macrophage)]−$B$×[Cytogenetic Risk Score]+$C$×[% BoneMarrow Blasts]

Probability Score$_{Drug\ B\ Response}$=$A$×[BAD Priming tumor cells]+$B$+[Age]−$C$×[Cytogenetic Risk Score]

Probability Score$_{Drug\ B\ Thrombocytopenia}$=$A$×[BID Priming(platlet cells)]+$B$+[Age]−$C$×[Cytogenetic Risk Score]

Probability Score$_{Drug\ C\ autoimmune\ reponse}$=$A$×[BID Priming (TH−17 cells)]+$B$+[Age]−$C$×[TH−17 cells]

Probability$_{Drug\ C\ Auto\ immune\ Response\ (RA)}$=$A$×[BIM Priming(TH−17 cells)−IM Priming (TH−17 cells)]+$B$+[Age]−$C$×[total THP-1 counts in synovia Hypothetical Report (Based on probability scores determined from algorithms):

| | |
|---|---|
| Patient Name | John Smith |
| Patient Birth Date | 7-7-1977 |
| Diagnosis | AML |
| Specimen ID | 1234567890 |

-continued

| | |
|---|---|
| Date/Time of Collection | 10-9-2017 14:20 |
| Assay | BH3 Profile |
| Assay Date | 10-10-2017 |
| Assay Status | Pass |
| Probability of Response to Cytarabine | High |
| Probability of Anemia after Cytarabine | Intermediate |
| Probability of Tumor Lysis Syndrome after Cytarabine | Low |
| Probability of Response to Azacitidine | Low |
| Etc. | Etc. |

Exemplary Clinical Factors and Additional Biomarkers

In some embodiments, the disclosure comprises the evaluation of clinical factors. In some embodiments, the disclosure comprises an evaluation of BH3 profiling and/or clinical factors to assess a patient response. In some embodiments, a clinical factor that provides patient response information in combination with a BH3 profiling study may not be linked to apoptosis. In some embodiments, a clinical factor is non-apoptosis affecting.

In one embodiment, the clinical factor is one or more of age, cytogenetic status, performance, histological subclass, gender, and disease stage.

In one embodiment, the clinical factor is age. In one embodiment, the patient age profile is classified as over about 10, or over about 20, or over about 30, or aver about 40, or over about 50, or aver about 60, or aver about 70, or over about 80 years old.

In one embodiment, the clinical factor is cytogenetic status. In some cancers, such as Wilms tumor and retinoblastoma, for example, gene deletions or inactivations are responsible for initiating cancer progression, as chromosomal regions associated with tumor suppressors are commonly deleted or mutated. For example, deletions, inversions, and translocations are commonly detected in chromosome region 9p21 in gliomas, non-small-cell lung cancers, leukemias, and melanomas. Without wishing to be bound by theory, these chromosomal changes may inactivate the tumor suppressor cyclin-dependent kinase inhibitor 2A. Along with these deletions of specific genes, large portions of chromosomes can also be lost. For instance, chromosomes 1p and 16q are commonly lost in solid tumor cells. Gene duplications and increases in gene copy numbers can also contribute to cancer and can be detected with transcriptional analysis or copy number variation arrays. For example, the chromosomal region 12q13-q14 is amplified in many sarcomas. This chromosomal region encodes a binding protein called MDM2, which is known to bind to a tumor suppressor called p53. When MDM2 is amplified, it prevents p53 from regulating cell growth, which can result in tumor formation. Further, certain breast cancers are associated with overexpression and increases in copy number of the ERBB2 gene, which codes for human epidermal growth factor receptor 2. Also, gains in chromosomal number, such as chromosomes 1q and 3q, are also associated with increased cancer risk.

Cytogenetic status can be measured in a variety of manners known in the art. For example, FISH, traditional karyotyping, and virtual karyotyping (e.g., comparative genomic hybridization arrays, CGH and single nucleotide polymorphism arrays) may be used. For example, FISH may be used to assess chromosome rearrangement at specific loci and these phenomena are associated with disease risk status. In some embodiments, the cytogentic status is favorable, intermediate, or unfavorable.

In one embodiment, the clinical factor is patient performance. Performance status can be quantified using any system and methods for scoring a patient's performance status are known in the art. The measure is often used to determine whether a patient can receive chemotherapy, adjustment of dose adjustment, and to determine intensity of palliative care. There are various scoring systems, including the Karnofsky score and the Zubrod score. Parallel scoring systems include the Global Assessment of Functioning (GAF) score, which has been incorporated as the fifth axis of the Diagnostic and Statistical Manual (DSM) of psychiatry Higher performance status (e.g., at least 80%, or at least 70% using the Karnofsky scoring system) may indicate treatment to prevent progression of the disease state, and enhance the patient's ability to accept chemotherapy and/or radiation treatment. For example, in these embodiments, the patient is ambulatory and capable of self care. In other embodiments, the evaluation is indicative of a patient with a low performance status (e.g., less than 50%, less than 30%, or less than 20% using the Karnofsky scoring system), so as to allow conventional radiotherapy and/or chemotherapy to be tolerated. In these embodiments, the patient is largely confined to bed or chair and is disabled even for self-care.

The Karnofsky score runs from 100 to 0, where 100 is "perfect" health and 0 is death. The score may be employed at intervals of 10, where: 100% is normal, no complaints, no signs of disease; 90% is capable of normal activity, few symptoms or signs of disease, 80% is normal activity with some difficulty, some symptoms or signs; 70% is caring for self, not capable of normal activity or work; 60% is requiring some help, can take care of most personal requirements; 50% requires help often, requires frequent medical care; 40% is disabled, requires special care and help; 30% is severely disabled, hospital admission indicated but no risk of death; 20% is very ill, urgently requiring admission, requires supportive measures or treatment; and 10% is moribund, rapidly progressive fatal disease processes.

The Zubrod scoring system for performance status includes: 0, fully active, able to carry on all pre-disease performance without restriction; 1, restricted in physically strenuous activity but ambulatory and able to carry out work of a light or sedentary nature, e.g., light house work, office work; 2, ambulatory and capable of all self-care but unable to can) out any work activities, up and about more than 50% a waking hours; 3, capable of only limited self-care, confined to bed or chair more than 50% of waking hours; 4, completely disabled, cannot carry on any self-care, totally confined to bed or chair; 5, dead.

In one embodiment, the clinical factor is a histological subclass. In some embodiments, histological samples of tumors are graded according to Elston & Ellis, Histopathology, 1991, 19:403-10, the contents of which are hereby incorporated by reference in their entirety.

In one embodiment, the clinical factor is gender. In one embodiment, the gender is male. In another embodiment the gender is female.

In one embodiment, the clinical factor is disease stage. By way of non-limiting example, using the overall stage grouping, Stage I cancers are localized to one part of the body; Stage II cancers are locally advanced, as are Stage III cancers. Whether a cancer is designated as Stage II or Stage III can depend on the specific type of cancer. In one non-limiting example, Hodgkin's disease, Stage II indicates affected lymph nodes on only one side of the diaphragm, whereas Stage III indicates affected lymph nodes above and below the diaphragm. The specific criteria for Stages II and III therefore differ according to diagnosis. Stage IV cancers have often metastasized, or spread to other organs or throughout the body.

In some embodiments, the clinical factor is the French-American-British (FAB) classification system for hematologic diseases (e.g. indicating the presence of dysmyelopoiesis and the quantification of myeloblasts and erythroblasts). In one embodiment, the FAB for acute lymphoblastic leukemias is L1-L3, or for acute myeloid leukemias is M0-M7.

In another embodiment, the method further comprises a measurement of an additional biomarker selected from mutational status, single nucleotide polymorphisms, steady state protein levels, and dynamic protein levels. In another embodiment, the method further comprises predicting a clinical response in the patient. In another embodiment, the clinical response is about 1, about 2, about 3, or about 5 year progression/event-free survival.

A variety of clinical factors have been identified, such as age profile and performance status. A number of static measurements of diagnosis have also been utilized, such as cytogenetics and molecular events including, without limitation, mutations in the genes MLL, AML/ETO, Flt3-ITD, NPM1 (NPMc+), CEBPα, IDH1, IDH2, RUNX1, ras, and WT1 and in the epigenetic modifying genes TET2 and ASXL, as well as changes in the cell signaling protein profile.

In some embodiments, the preventive methods comprise administering a treatment to a patient that is likely to be afflicted by cancer as guided by the methods described herein. In some embodiments, a subject is likely to be afflicted by cancer if the subject is characterized by one or more of a high risk for a cancer, a genetic predisposition to a cancer (e.g. genetic risk factors), a previous episode of a cancer (e.g. new cancers and/or recurrence), a family history of a cancer, exposure to a cancer-inducing agent (e.g. an environmental agent), and pharmacogenomic information (the effect of genotype on the pharmacokinetic, pharmacodynamic or efficacy profile of a therapeutic).

In some embodiments, a subject is likely to be afflicted by cancer if the subject is characterized by a high risk for a cancer. In some embodiments, a subject is likely to be afflicted by cancer if the subject is characterized by a genetic predisposition to a cancer. In some embodiments, a genetic predisposition to a cancer is a genetic clinical factor, as is known in the art. Such clinical factors may include, by way of example, HNPCC, MLH1, MSH2, MSH6, PMS1, PMS2 for at least colon, uterine, small bowel, stomach, urinary tract cancers. In some embodiments, a subject is likely to be afflicted by cancer if the subject is characterized by a previous episode of a cancer. In some embodiments, the subject has been afflicted with 1, or 2, or 3, or 4, or 5, or 6, previous episodes of cancer. In some embodiments, a subject is likely to be afflicted by cancer if the subject is characterized by a family history of a cancer. In some embodiments, a parent and/or grandparent and/or sibling and/or aunt/uncle and/or great aunt/great uncle, and/or cousin has been or is afflicted with a cancer. In some embodiments, a subject is likely to be afflicted by cancer if the subject is characterized by exposure to a cancer-inducing agent (e.g. an environmental agent). For example, exposing skin to strong sunlight is a clinical factor for skin cancer. By way of example, smoking is a clinical factor for cancers of the lung, mouth, larynx, bladder, kidney, and several other organs.

Further, in some embodiments, the any one of the following clinical factors may be useful in the methods described herein: gender; genetic risk factors; family history; personal history; race and ethnicity; features of the certain tissues; various benign conditions (e.g. non-proliferative lesions); previous chest radiation; carcinogen exposure and the like.

Further still in some embodiments, the any one of the following clinical factors may be useful in the methods described herein: one or moo of a cell surface marker M33, a cell surface marker CD34, a FLT3 mutation status, a p53 mutation status, a phosphorylation state of MEK-1 kinase, and phosphorylation of serine at position 70 of Bcl-2.

In some embodiments, the clinical factor is expression levels of the cytokines, including, without limitation, interleukin-6. In some embodiments, interleukin-6 levels will correlate with likelihood of response in MM patients, including a poor patient prognosis or a good patient prognosis.

In certain embodiments, the likelihood of response is determined by assessing a percent priming. In certain embodiments, the priming is defined by the following equation:

$$\% \text{ Priming} = \left[100 * \left(\frac{DMSO\ AUC - Peptide_1\ AUC}{DMSO\ AUC - CCCP_{avg}AUC}\right)\right]Peptide_1 +$$
$$\left[100 * \left(\frac{DMSO\ AUC - Peptide_2 AUC}{DMSO\ AUC - CCCP_{avg}AUC}\right)\right]Peptide_2 + \ldots\ /(n\ \text{peptides})$$

in which the AUC comprises either area under the curve or signal intensity; the DMSO comprises the baseline negative control; and the CCCP (Carbonyl cyanide m-chlorophenyl hydrazone) comprises an effector of protein synthesis by serving as uncoupling agent of the proton gradient established during the normal activity of electron carriers in the electron transport chain in the mitochondria comprises the baseline positive control. In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS). In some embodiments, the signal intensity is a single time point measurement that occurs between about 5 min and about 300 min.

In another embodiment, the method comprises measuring the BH3 profiling assay and one or more of a cell surface marker CD33, a cell surface marker CD34, FLT3 mutation status, a p53 mutation status, a phosphorylation state of MEK-1 kinase, and phosphorylation of serine at position 70 of Bcl-2; and correlating to efficacy in treating AML patients with cytarabine or cytarabine-based chemotherapy and/or azacytidine.

In another embodiment, the method comprises measuring the BH3 profiling assay and one or more of a cell surface marker CD33, a cell surface marker CD34, a FLT3 mutation status, a p53 mutation status, a phosphorylation state of MEK-1 kinase, and phosphorylation of serine at position 70 of Bcl-2; and correlating to efficacy in treating MM patients with chemotherapy.

In still another embodiment, the cancer is AML and/or MM and the clinical factor is age profile and/or cytogenetic status; or the cancer is AML and/or MM and the cancer treatment is cytarabine or cytarabine-based chemotherapy and/or azacytidine, or the cancer treatment is cytarabine or cytarabine-based chemotherapy and/or azacytidine and the clinical factor is age profile and/or cytogenetic status, or the cancer treatment is cytarabine or cytarabine-based chemotherapy and/or azacytidine; the cancer is AML and/or MM; and the clinical factor is age profile and/or cytogenetic status.

The disclosure also provides kits that can simplify the evaluation of tumor or cancer cell specimens. A typical kit of the disclosure comprises various reagents including, for example, one or more agents to detect a BH3 peptide. A kit may also comprise one or more of reagents for detection, including those useful in various detection methods, such as, for example, antibodies. The kit can further comprise materials necessary for the evaluation, including welled plates, syringes, and the like. The kit can further comprise a label or printed instructions instructing the use of described reagents. The kit can further comprise an treatment to be tested.

It should be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes. All numerical ranges should be understood to include each and every numerical point within the numerical range, and should be interpreted as reciting each and every numerical point individually. The endpoints of all ranges directed to the same component or property are inclusive, and intended to be independently combinable.

The term "about" when used in connection with a referenced numeric indication means the referenced numeric indication plus or minus up to 10% of that referenced numeric indication. For example, the language "about 50" covers the range of 45 to 55.

As used herein, the word "include," and, its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

EXAMPLES

Example 1

BH3 Profiling

Thawed aliquots of pretreatment peripheral blood mononuclear cells containing B cell chronic lymphogenous leukemia cells were purified for untouched B-cells by non-B-cell depletion using a cocktail of biotinylated monoclonal Abs (CD2, CD4, CD11b, CD16, CD36, Anti-IgE, and CD235a (glycophorin) and magnetic beads (Miltenyi Biotec, Auburn, Calif.). The extent of cell purification was monitored by flow cytometry of stained cells before and after purification with anti-CD19-APC and anti-biotin antibody-FITC for the presence of non-B cells labeled with MAbs from depletion cocktail Miltenyi Biotec, Auburn, Calif.). Specimens were permeabilized with digitonin and incubated with JC-1 mitochondrial dye and 100 µM BH3 peptides (Bim, Puma, Noxa, Bad, Bmf, Hrk; Bim and Puma were also assayed at 0.1 µM and 10 µM, respectively) or with dimethyl sulfoxide (DMSO [(1%)] or Carbonyl cyanide m-chlorophenyl hydrazone (CCCP [10 µM]). Samples were run in triplicate and fluorescent traces of JC-1, dye monitored over 300 min of assay. Area under the curve was integrated relative to the positive control uncoupling reagent after normalization for DMSO background:

$$\% \text{ priming} = \left(1 - \left(\frac{\text{Peptide} - CCCP}{DMSO - CCCP}\right)\right) \times 100$$

Statistical Analysis

Univariate testing association between biomarker status (% priming) and clinical response classification or Tumor Lysis Syndrome (TLS) was by regression (more than 2 groups compared) or by logistic regression analysis (when two groups were analyzed). We pre-determined a statistical analysis plan with significance of $p<0.05$. Marker predictive ability was assessed using the area under the receiver operator characteristic curve (AUC). Multivariate analyses were performed using logistic regression and significant adjustment variables from patient clinicopathologic data, Analyses utilized SAS software, version 9.2 (Cary, N.C.), R version 2.14.2 (Vienna, Austria), and/or Graphpad Prism version 5.04 (La Jolla, Calif.).

Example 2

BH3 Profiling of Pre-Treatment Patient Specimens

From 26 study participants (median age of 73.8 years [range: 61.1-80.7 years], aliquots of pre-treatment specimens were thawed for the purpose of BH3 profiling. Upon thawing, these specimens yielded cells with excellent viability (median of 82.1% [range: 62.2-97.9%] live cells), They were then subjected to in vitro exposure to individual BH3 peptides, including, an activator (Bim) and several sensitizers (Noxa, Puma, Bad, Hrk, Bmf) as surrogates for the function of Bcl-1 family proteins. Twenty-three of 26 tested specimens (n=8 and n=15 from BM and PB, respectively) provided analyzable data, for an overall technical success rate of 88.5%. Three samples were eliminated from statistical analysis due to insufficient cell numbers. Of note, 13 specimens were analyzed in duplicate, with an overall Coefficient of Variation (CV) for repeat samples from individual patients being generally between 3-5%, indicative of a technically robust assay (data not shown).

Figure 1A:
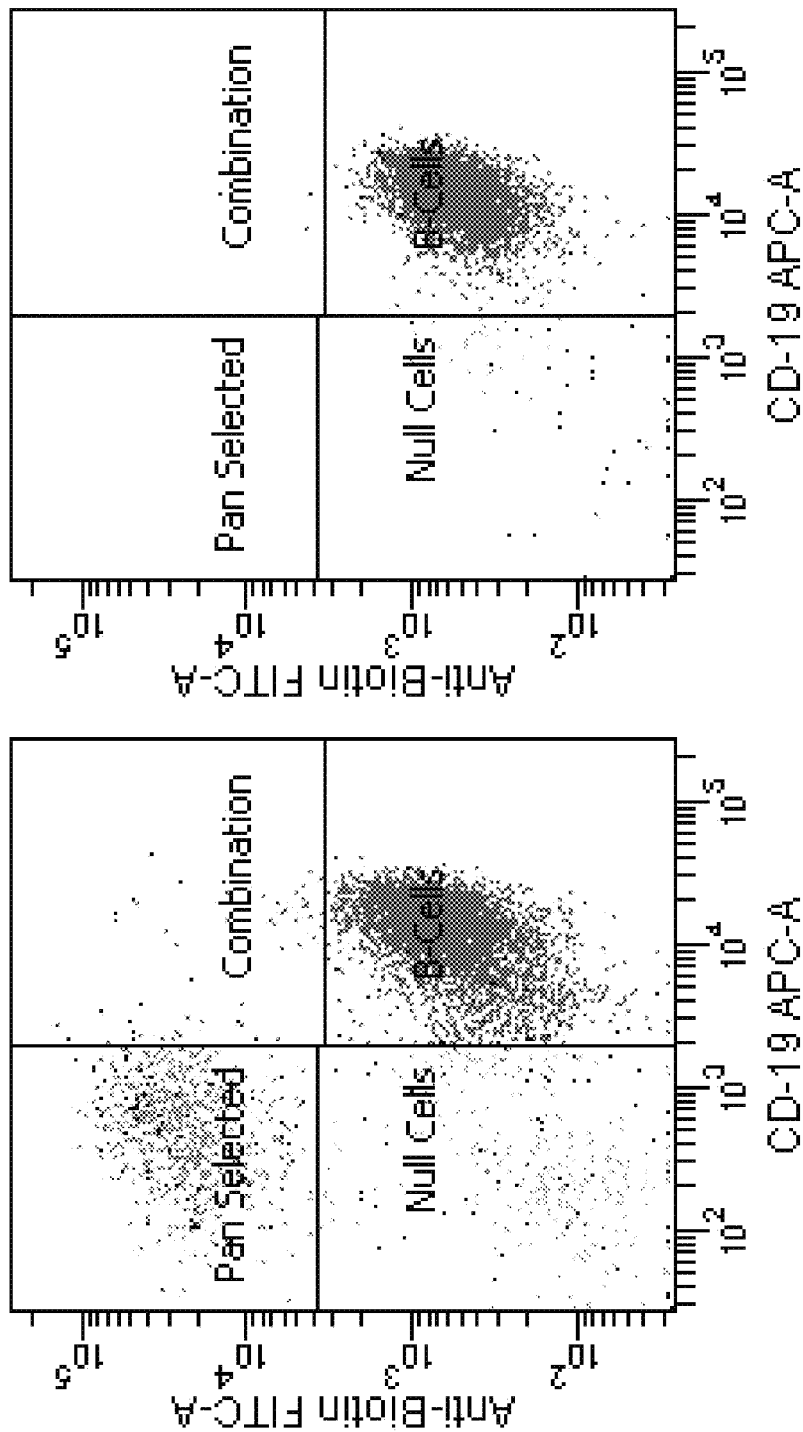
FIG. 1A-C is a series of graphs showing untouched B-cell isolation and representative BH3 profiling readout data. C-cell CLL cells were isolated from patient PBMC specimens taken before therapeutic administration. An Ab cocktail was used to label the non-B cells while CD19+ defined the B-cell population. Flow cytometry (Panel A) indicated that in most instances, CLL cell purification post bead separation generally achieved greater than 99% purity to which to hone the BH3 profiling signal in subsequent downstream assay. Two representative patient specimen BH3 profiling data readouts (Panels B and C) are indicated as a typical highly primed as well as a poorly primed specimen, respectively.
Figure 1B:
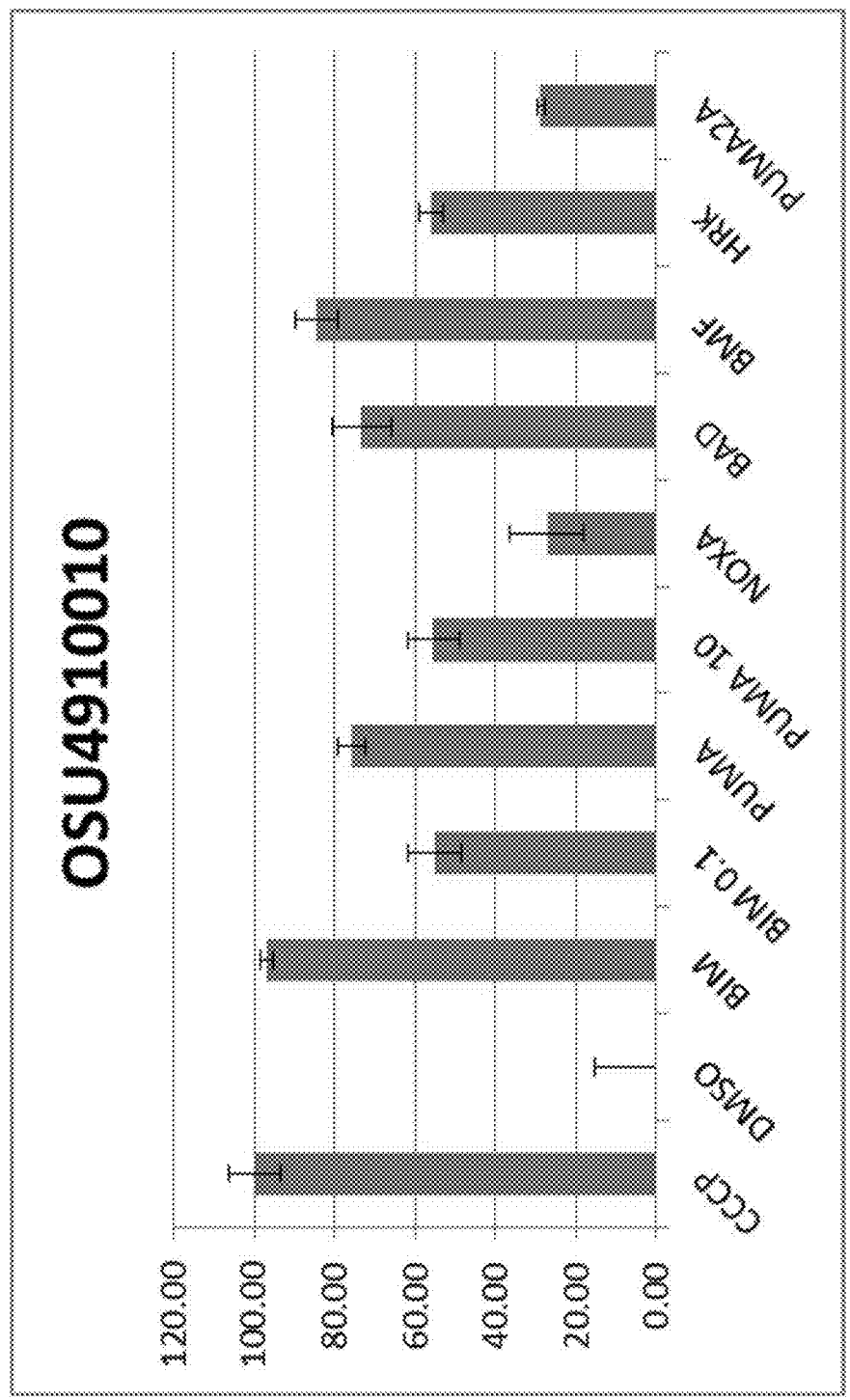
Figure 1C:
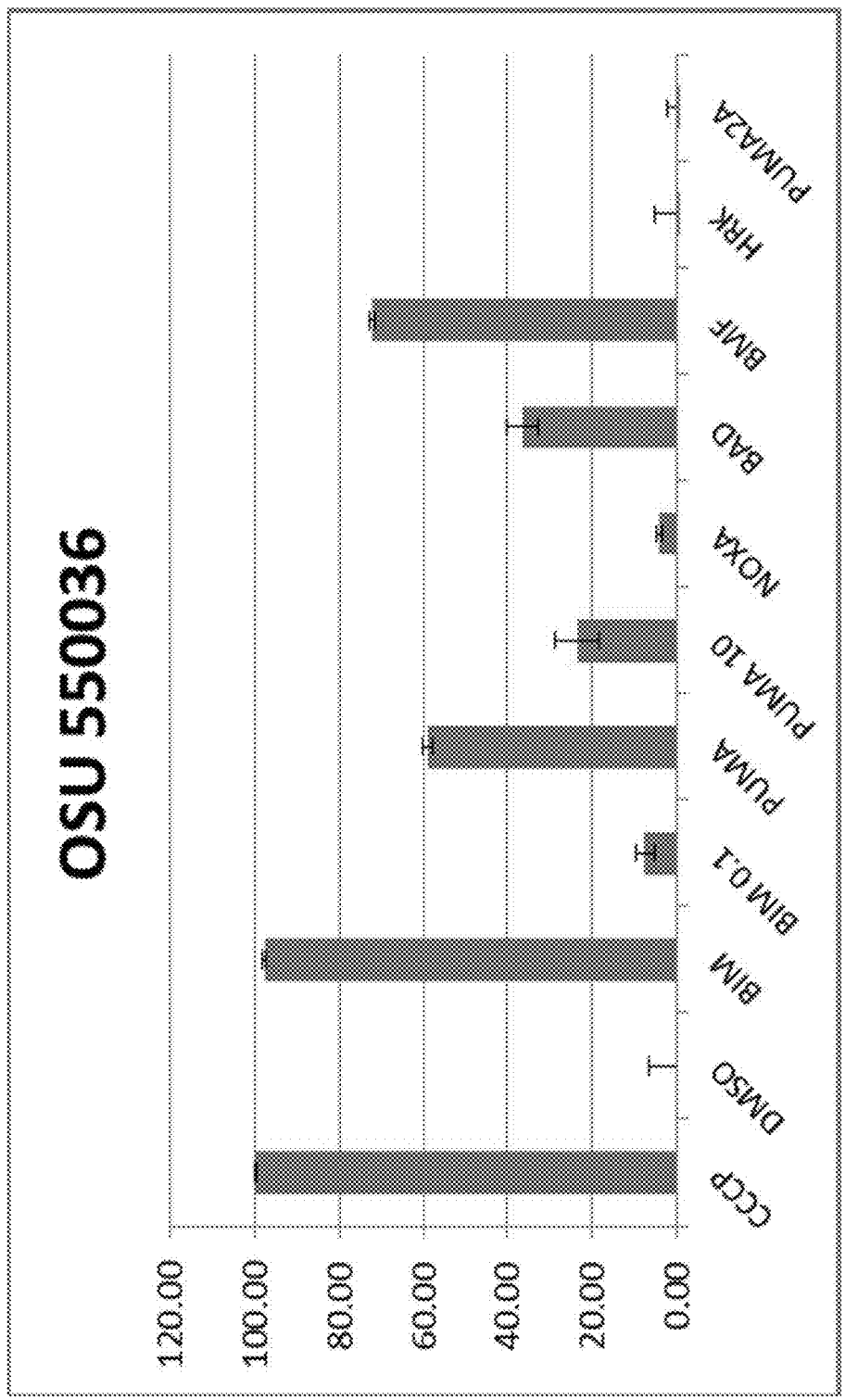

Association Between Priming to BH3 Peptides and Response to Induction Therapy with Vorinostat/GO The percent priming, i.e. quantifiable propensity of a given BH3 peptide or BH3 mimetic compound to induce mitochondrial depolarization relative to an uncoupling control agent, for each peptide is summarized in Table 2 separately for patients who responded to study therapy (i.e. achieved either CR/CRp) and those who failed treatment. Among the peptides assayed, only Noxa elicited a statistically significantly different priming between responders (54.1±29.0% [mean±LSD]) and non-responders (23.8±14.9%; p=0.027); the percent priming with Noxa for individual patients is depicted in FIG. 1A. To test the ability of Noxa to serve as predictive biomarker, we employed the area under the receiver operator characteristic curve (AUC) to analyze the sensitivity and specificity of this biomarker, which yielded an AUC of 0.83 (95% CI: 0.65-1.00;

p=0.00042; FIG. 1B). Because we found responders to be significantly younger than non-responders (see Table 1), we performed adjusted analyses of Noxa priming in which we accounted for age as second covariate. As shown in FIG. 1B, adjustment for age as a continuous variable) improved the AUC to 0.88 (95% CI: 0.75-1.00) In contrast to Noxa, no statistically significant differences were found for priming induced with Bim (at 2 peptide concentrations), Puma (at 2 peptide concentrations), Bad, Hrk, and Bmf (Table 2).

Example 3

Association Between Priming to BH3 Peptides or BH3 Mimetic Compounds in Platelets as a Biomarker for Thrombocytopenia Thawed aliquots of pretreatment peripheral blood mononuclear cells containing erythroblast cells are prepared for BH3 profiling as described above with the following distinctions that enable measurements to be rendered from the erythroblast populations;

Cells are washed and resuspended in 200 µl of PBS containing 4% FBS for immunostaining. For analysis of erythroid differentiation, cells are incubated with 1:200 dilution of phycoerythrin-conjugated anti-CD71 (BD Biosciences) and allophycocyanin-conjugated anti-Ter-119 antibody (BD Biosciences) for 15 min at room temperature. For enucleation analysis, cells are additionally stained with 10 µg/ml Hoechst 33342 (Sigma) at room temperature for 15 min. Propidium iodide (BD Biosciences) at a final concentration of 0.2 µg/ml is added to exclude dead cells from the analysis. Apoptosis is evaluated by co-staining with allophycocyanin-conjugated annexin V (BD Biosciences) and propidium iodide. To perform cell cycle analysis, the cells are washed and resuspended in 50 µl of PBS, fixed in 1 ml of cold 90% ethanol, and stored at 4° C. overnight. The fixed cells are washed and incubated in PBS containing propidium iodide (20 µg/ml) and RNase-A (200 µg/ml) for 1 h at room temperature. Flow cytometry is performed using BD LSRII (BD Biosciences), and data analysis carried out using BD FACSDiva (BD Biosciences).

The association between priming to BH3 peptides or BH3 mimetic compounds and response to treatment with panobinostat, Navitoclax, Methotrexate or carboplatin is established by performing variable regression analysis.

The percent priming, i.e. quantifiable propensity of a given BH3 peptide or BH3 mimetic compound to induce mitochondrial depolarization relative to an uncoupling control agent, for each peptide is summarized.

Example 4

Association Between Priming to BH3 Peptides or BH3 Mimetic Compounds in Erythroblasts as a Biomarker for Onset of Anemia Thawed aliquots of pretreatment peripheral blood mononuclear cells containing erythroblast cells are prepared for BH3 profiling as described above with the following distinctions that enable measurements to be rendered from the erythroblast populations;

Cells are washed and resuspended in 200 µl of PBS containing 4% FBS for immunostaining. For analysis of erythroid differentiation, cells are incubated with 1:200 dilution of phycoerythrin-conjugated anti-CD71 (BD Biosciences) for 15 min at room temperature. For enucleation analysis, cells are additionally stained with 10 µg/ml Hoechst 34580 (Life Technologies) at room temperature for 15 min. Apoptosis is evaluated by co-staining with allophycocyanin-conjugated annexin V (BD Biosciences) and propidium iodide (BD Biosciences) at a final concentration of 0.2 µg/ml is added to exclude dead cells from the analysis. Flow cytometry is performed using BD FACSCanto II (BI) Biosciences), and data analysis was carried out using BD FACSDiva (BD Biosciences).

The association between priming to BH3 peptides or BH3 mimetic compounds and response to treatment with anti-tumor therapies, for instance, Velcade in combination with revlamid and dexamethasone, or carlfizomib in combination with palmolidomide is established.

Example 5

Association Between Priming to BH3 Peptides or BH3 Mimetic Compound in Macrophages as a Biomarker for Onset of Colitis or Rheumatoid Arthritis.

Thawed aliquots of pretreatment peripheral blood mononuclear cells containing erythroblast cells are prepared for BH3 profiling as described above with the following distinctions that enable measurements to be rendered from the macrophage populations;

Cells are washed and resuspended in 200 µl of PBS containing 4% FBS for immunostaining. For analysis of erythroid differentiation, cells are incubated with 1:200 dilution of Screen suspension THP-1 cells (monocytes) stained with the BD Lyoplate human cell surface marker screening panel (Becton Dickenson) using flow cytometry. Annexin V (BD Biosciences) and propidium iodide (BD Biosciences at a final concentration of 0.2 µg/ml is added to exclude dead cells from the analysis. Flow cytometry was performed using BD FACSCanto II (BD Biosciences), and data analysis was carried out using BD FACSDiva, (BD Biosciences).

Association between Priming to BH3 Peptides or BH3 mimetic compounds and Response to treatment with anti-tumor therapies that rely on mediating an immune response against the tumor, for instance, Yervoy (ipilimumab) used alone or in combination with anti-PDL-1 (MPDL3280A, Genentech).

TABLE 1

| | | CLL Patients Clinicalpathologic Information | | | | | | |
|---|---|---|---|---|---|---|---|---|
| | | 2 Categories of Response | | | 3 Categories of Response | | | |
| | | PD/SD | PR | p-value | PD | SD | PR | p-value |
| Age (Range 38-84 years) | Median(±SD) | 62.4 (8.8) | 61.6 (12.0) | 0.96 | 60.7 (11.2) | 63.3 (7.3) | 61.6 (12.0) | 0.74 |
| Gender | Male | 31 (50.0%) | 17 (27.4%) | 0.51 | 12 (19.4%) | 19 (30.6%) | 17 (27.4%) | 0.46 |
| | Female | 6 (9.7%) | 6 (9.7%) | | 1 (1.6%) | 5 (8.1%) | 6 (9.7%) | |
| | NA | 2 (3.2%) | 0 (0.0%) | | 1 (1.6%) | 1 (1.6%) | 0 (0.0%) | |
| Race | caucasian | 32 (51.6%) | 20 (32.3%) | 1 | 9 (14.5%) | 23 (37.1%) | 20 (32.3%) | 0.062 |
| | other | 5 (8.1%) | 3 (4.8%) | | 4 (6.5%) | 1 (1.6%) | 3 (4.5%) | |
| | NA | 2 (3.2%) | 0 (0.0%) | | 1 (1.6%) | 1 (1.6%) | 0 (0.0%) | |

TABLE 1-continued

CLL Patients Clinicalpathologic Information

|  |  | 2 Categories of Response | | | 3 Categories of Response | | | |
|---|---|---|---|---|---|---|---|---|
|  |  | PD/SD | PR | p-value | PD | SD | PR | p-value |
| Baseline ECOG | 0 | 11 (17.7%) | 3 (4.8%) | 0.30 | 5 (8.1%) | 6 (9.7%) | 3 (4.8%) | 0.55 |
|  | 1 | 22 (35.4%) | 16 (25.8%) |  | 6 (9.7%) | 16 (25.8%) | 16 (25.8%) |  |
|  | 2 | 5 (8.1%) | 3 (4.8%) |  | 2 (3.2%) | 3 (4.8%) | 3 (4.8%) |  |
|  | NA | 2 (3.2%) | 1 (1.6%) |  | 1 (1.6%) | 1 (1.6%) | 1 (1.6%) |  |
| RAI score | I | 1 (1.6%) | 4 (6.5%) | 0.25 | 0 (0.0%) | 1 (1.6%) | 4 (6.5%) | 0.032 |
|  | II | 2 (3.2%) | 2 (3.2%) |  | 1 (1.6%) | 1 (1.6%) | 2 (3.2%) |  |
|  | III | 6 (9.7%) | 3 (4.8%) |  | 5 (8.1%) | 1 (1.6%) | 3 (4.8%) |  |
|  | IV | 27 (43.5%) | 14 (22.6%) |  | 6 (9.7%) | 21 (33.9%) | 14 (22.8%) |  |
|  | NA | 3 (4.8%) | 0 (0.0%) |  | 2 (3.2%) | 1 (1.6%) | 0 (0.0%) |  |
| Splenomegaly | Yes | 15 (24.2%) | 7 (11.3%) | 0.58 | 4 (6.5%) | 11 (17.7%) | 7 (11.3%) | 0.51 |
|  | No | 22 (35.4%) | 16 (25.8%) |  | 9 (14.5%) | 13 (21.0%) | 16 (25.5%) |  |
|  | NA | 2 (3.2%) | 0 (0.0%) |  | 1 (1.6%) | 1 (1.6%) | 0 (0.0%) |  |
| Hepatomegaly | Yes | 5 (8.1%) | 1 (1.6%) | 0.38 | 2 (3.2%) | 3 (4.8%) | 1 (1.6%) | 0.37 |
|  | No | 24 (38.7%) | 17 (27.4%) |  | 6 (9.7%) | 18 (29.0%) | 17 (27.4%) |  |
|  | NA | 10 (16.1%) | 5 (8.1%) |  | 6 (9.7%) | 4 (5.5%) | 5 (8.1%) |  |
| 11q (ATM) del | Yes | 8 (12.9%) | 8 (12.9%) | 0.53 | 4 (6.5%) | 4 (6.5%) | 8 (12.9%) | 0.44 |
|  | No | 18 (29.0%) | 11 (17.7%) |  | 5 (8.1%) | 13 (21.0%) | 11 (17.7%) |  |
|  | NA | 11 (17.7%) | 6 (9.7%) |  | 3 (4.8%) | 5 (12.9%) | 6 (9.7%) |  |
| trisomy 12 | Yes | 1 (1.6%) | 7 (11.3%) | 0.0064 | 0 (0.0%) | 1 (1.6%) | 7 (11.3%) | 0.022 |
|  | No | 25 (40.3%) | 12 (19.4%) |  | 9 (14.5%) | 15 (25.8%) | 12 (19.4%) |  |
|  | NA | 13 (21.0%) | 4 (6.5%) |  | 5 (8.1%) | 8 (12.9%) | 4 (6.5%) |  |
| del 13 q | Yes | 17 (27.4%) | 9 (14.5%) | 0.23 | 7 (11.3%) | 10 (16.1%) | 9 (14.5%) | 0.14 |
|  | No | 9 (14.5%) | 10 (16.1%) |  | 2 (3.2%) | 7 (11.3%) | 10 (16.1%) |  |
|  | NA | 13 (21.0%) | 4 (6.5%) |  | 5 (8.1%) | 8 (12.9%) | 4 (6.5%) |  |
| 17p (p53) del | Yes | 9 (14.5%) | 8 (12.9%) | 0.35 | 2 (3.2%) | 5 (8.1%) | 8 (12.9%) | 0.55 |
|  | No | 19 (30.6%) | 11 (17.7%) |  | 7 (11.3%) | 12 (19.4%) | 11 (17.7%) |  |
|  | NA | 13 (21.0%) | 4 (6.5%) |  | 5 (8.1%) | 8 (12.9%) | 4 (6.5%) |  |
| chro 3 complex | Yes | 4 (6.5%) | 4 (6.5%) | 0.70 | 3 (4.8%) | 1 (1.6%) | 4 (6.5%) | 0.18 |
|  | No | 22 (35.4%) | 15 (24.2%) |  | 6 (9.7%) | 16 (25.8%) | 15 (24.2%) |  |
|  | NA | 13 (21.0%) | 4 (6.5%) |  | 5 (8.1%) | 8 (12.9%) | 4 (6.5%) |  |

TABLE 2

BH3 profiling biomarkers discriminate
clinical response to alvocidib treatment
Proof-of-principle, validation, and combined data sets

|  |  | Regression pvalue (PD v SD v PR) | AUC | AUC pvalue (95% CI) | PFS pvalue | OS pvalue |
|---|---|---|---|---|---|---|
| Principle (n = 30) | BIM(0.1) | 0.014 | 0.77 | 0.00015 [.63, .90] | 0.15 | 0.039 |
|  | PUMA(10) | 0.18 | 0.62 | 0.13 [.47, .76] | 0.38 | 0.55 |
|  | NOXA | 0.97 | 0.57 | 0.40 [.41, .74] | 0.85 | 0.39 |
|  | BAD | 0.79 | 0.55 | 0.63 [.36, .73] | 0.61 | 0.85 |
|  | BMF | 0.30 | 0.53 | 0.77 [.36, .69] | 0.94 | 0.77 |
|  | HRK | 0.0098 | 0.73 | 0.00035 [.60, .85] | 0.34 | 0.41 |
| Validation (n = 32) | BIM(0.1) | 0.0051 | 0.75 | 0.00032 [.62, .89] | 0.30 | 0.27 |
|  | PUMA(10) | 0.20 | 0.62 | 0.2 [.44, .79] | 0.88 | 0.95 |
|  | NOXA | 0.21 | 0.59 | 0.21 [.45, .74] | 0.72 | 0.95 |
|  | BAD | 0.38 | 0.57 | 0.5 [.37, .76] | 0.40 | 0.50 |
|  | BMF | 0.98 | 0.52 | 0.84 [.35, .68] | 0.99 | 0.79 |
|  | HRK | 0.015 | 0.72 | 0.0043 [.57, .87] | 0.58 | 0.51 |
| All patients (n = 62) | BIM(0.1) | 0.0027 | 0.72 | 0.0000014 [.63, .81] | 0.25 | 0.066 |
|  | PUMA(10) | 0.059 | 0.62 | 0.031 [.51, .73] | 0.71 | 0.87 |
|  | NOXA | 0.65 | 0.57 | 0.22 [.46, .68] | 0.60 | 0.39 |
|  | BAD | 0.64 | 0.54 | 0.51 [.42, .67] | 0.67 | 0.36 |
|  | BMF | 0.69 | 0.50 | 0.96 [.39, .61] | 0.87 | 0.91 |
|  | HRK | 0.00046 | 0.71 | 0.000040 [.61, .81] | 0.083 | 0.78 |

TABLE 3

BH3 profiling biomarkers discriminate patients with tumor lysis syndrome (TLS) to alvocidib treatment

| | Correlation with Tumor Lysis Syndrome | | | |
|---|---|---|---|---|
| | wilcoxon.pvalue | log.regress.pvalue | AUC | AUC.pvalue [CI] |
| Age | 0.034 | 0.067 | 0.70 | 0.027[.52, .55] |
| Baseline.ECOG | 0.021 | 0.031 | 0.68 | 0.0017[.57, .80] |
| BMI.0.1 | 0.18 | 0.45 | 0.63 | 0.10[.47, .78] |
| PUMA.10 | 0.0083 | 0.012 | 0.75 | 0.00079[.60, .90] |
| NOXA | 0.45 | 0.10 | 0.57 | 0.47[.37, .78] |
| BAD | 0.0080 | 0.012 | 0.75 | 0.00072[.60, .89] |
| HRK | 0.28 | 0.37 | 0.60 | 0.21[.44, .77] |
| Gender | 1.00 | 0.69 | 0.53 | 0.66[.41, .63] |
| Race | 1.00 | 0.53 | 0.54 | 0.46[.44, .63] |
| Stage.using.Rai | 0.072 | 0.062 | 0.66 | 0.0049 [.55, .77] |
| Splenomegaly | 0.18 | 0.13 | 0.62 | 0.12[.47, .78] |
| Hepatomegaly | 1.00 | 0.74 | 0.52 | 0.75[.41, .63] |
| ATM.deletion | 0.27 | 0.23 | 0.60 | 1[.45, .76] |
| X12cen.three.copies | 0.64 | 0.38 | 0.56 | 1[.44, .68] |
| D13s319.deletion . . . 13q14. | 0.47 | 0.37 | 0.58 | 0.33[.41, .75] |
| D13s319.deletion.of.both.alleles . . . nullisomy.13q14. | 0.47 | 0.37 | 0.58 | 0.33[.41, .75] |
| p53.deletion . . . 17q13. | 0.70 | 0.50 | 0.56 | 1[.39, .72] |
| Bcl6.three.copies . . . 3q27. | 1.00 | 0.97 | 0.50 | 0.96[.40, .60] |

What is claimed:

1. An in vitro method for treating a chronic lymphocytic leukemia (CLL) patient, comprising:
   (a) determining in vitro a likelihood of an adverse response to one or more cancer treatments; the determination comprising performing BH3 profiling of a cell specimen from the patient, wherein the BH3 profiling comprises:
      (i) permeabilizing an aliquot of cells from the cell specimen from the patient;
      (ii) contacting the aliquot of permeabilized cells with a BH3 domain peptide, wherein the BH3 domain peptide is at least one of BAD and PUMA peptides;
      (iii) measuring the BH3 domain peptide-induced mitochondrial outer membrane permeabilization (MOMP) in the aliquot of cells to determine the BH3 profile, wherein:
         the BH3 profile indicates an association between the at least one of BAD and PUMA peptides and the patient likelihood of the adverse response to the one or more cancer treatments, the association being established by performing Receiver Operator Characteristic (ROC)- plot analysis, wherein an area under the curve for the ROC plot analysis above 0.75 for the at least one of BAD and PUMA peptides indicates a high risk of the patient likelihood of the adverse response to the one or more cancer treatments; wherein the one or more cancer treatments comprise treatment of the CLL patient with a cyclin-dependent kinase inhibitor;
   (b) classifying the patient for likelihood of the adverse response to one or more cancer treatments, wherein the adverse response comprises tumor lysis syndrome (TLS), and
   (c) administering the cyclin-dependent kinase inhibitor to a patient who is not classified as likely to have the TLS response.

2. The method of claim 1, wherein a high likelihood of an adverse response to one or more cancer treatments directs treatment that comprises withholding of the one or more cancer treatments causing the adverse response.

3. The method of claim 1, wherein a high likelihood of an adverse response to one or more cancer treatments directs treatment that comprises administering one or more cancer treatments that do not comprise the one or more cancer treatments causing the adverse response.

4. The method of claim 1, further comprising determining one or more clinical factors of the patient.

5. The method of claim 4, wherein the one or more clinical factors are selected to increase specificity and/or sensitivity of the BH3 profile for association with an adverse response.

6. The method of claim 4, wherein the clinical factor is one or more of age, cytogenetic risk status, performance, histological subclass, gender, Eastern Cooperative Oncology Group (ECOG) status, and disease stage.

7. The method of claim 4, wherein the clinical factor is one or more of ECOG status and patient age.

8. The method of claim 1, wherein a low likelihood of an adverse response to one or more cancer treatments directs an evaluation of a therapeutic efficacy to the one or more cancer treatments; wherein the evaluation comprises classifying the patient for likelihood of a therapeutic efficacy to one or more cancer treatment.

9. The method of claim 8, wherein the BH3 profile for likelihood of a therapeutic efficacy to one or more cancer treatment comprises measuring levels of BIM and/or HRK.

10. The method of claim 8, wherein the therapeutic efficacy comprises a high clinical response and/or a high overall survival.

11. The method of claim 4, wherein the one or more clinical factors are selected to increase specificity and/or sensitivity of the BH3 profile for association with therapeutic efficacy.

12. The method of claim 4, wherein the clinical factor is trisomy 12 status.

13. The method of claim 1, further comprising measurement of an additional biomarker selected from mutational status, single nucleotide polymorphisms, steady state protein levels, and dynamic protein levels.

14. The method of claim 1, wherein the BH3 profiling is performed on purified B cells from the CLL patient.

* * * * *